(12) United States Patent
Okada et al.

(10) Patent No.: US 12,066,433 B2
(45) Date of Patent: Aug. 20, 2024

(54) METHOD FOR ANALYZING TEST SUBSTANCE, ANALYZER, TRAINING METHOD, ANALYZER SYSTEM, AND ANALYSIS PROGRAM

(71) Applicants: SYSMEX CORPORATION, Kobe (JP); OSAKA UNIVERSITY, Suita (JP); NATIONAL INSTITUTE OF ADVANCED INDUSTRIAL SCIENCE AND TECHNOLOGY, Tokyo (JP)

(72) Inventors: Masaya Okada, Kobe (JP); Yuki Shimaoka, Kobe (JP); Shigeki Iwanaga, Kobe (JP); Kazuki Bando, Suita (JP); Katsumasa Fujita, Suita (JP); Yasunori Nawa, Ikeda (JP); Satoshi Fujita, Ikeda (JP)

(73) Assignees: SYSMEX CORPORATION, Kobe (JP); OSAKA UNIVERSITY, Osaka (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 17/686,802

(22) Filed: Mar. 4, 2022

(65) Prior Publication Data
US 2022/0283083 A1    Sep. 8, 2022

(30) Foreign Application Priority Data

Mar. 5, 2021    (JP) ................................ 2021-035593
Mar. 5, 2021    (JP) ................................ 2021-035597

(51) Int. Cl.
*G01N 21/65*    (2006.01)
*G01N 21/25*    (2006.01)
(Continued)

(52) U.S. Cl.
CPC ..... *G01N 33/54353* (2013.01); *G01N 21/255* (2013.01); *G01N 21/314* (2013.01);
(Continued)

(58) Field of Classification Search
CPC .. G01N 21/255; G01N 21/314; G01N 21/658; G01N 2201/121;
(Continued)

(56) References Cited

U.S. PATENT DOCUMENTS 8,385,615 B2 * 2/2013 Levenson .......... G01N 21/6486
600/407
10,801,964 B2 * 10/2020 Lednev ................ G01N 21/658
(Continued)

FOREIGN PATENT DOCUMENTS

CN    111033230 A  *  4/2020  ............. G01N 21/35
JP    4-163600 A     6/1992
(Continued)

OTHER PUBLICATIONS

Lu, Taiwei and Lerner, Jeremy, "Spectroscopy and Hybrid Neural Network Analysis", IEEE, vol. 84 no. 6 (Year: 1996).*
(Continued)

*Primary Examiner* — Michelle M Iacoletti
*Assistant Examiner* — Noah J. Haney
(74) *Attorney, Agent, or Firm* — Sughrue Mion, PLLC

(57) ABSTRACT

Disclosed is an analytical method for analyzing a test substance contained in a measurement sample, the method comprising: generating a data set based on a plurality of optical spectra acquired from a plurality of locations in the measurement sample; inputting the data set into a deep learning algorithm having a neural network structure; and outputting information on the test substance, on the basis of an analytical result from the deep learning algorithm.

20 Claims, 23 Drawing Sheets

(51) Int. Cl.
*G01N 21/31* (2006.01)
*G01N 33/543* (2006.01)
*G01N 33/58* (2006.01)
*G01N 33/68* (2006.01)
*G06N 3/08* (2023.01)
*G16C 20/20* (2019.01)
*G16C 20/70* (2019.01)

(52) U.S. Cl.
CPC ..... *G01N 21/658* (2013.01); *G01N 33/54346* (2013.01); *G01N 33/588* (2013.01); *G01N 33/6812* (2013.01); *G06N 3/08* (2013.01); *G16C 20/20* (2019.02); *G01N 2201/121* (2013.01); *G01N 2201/1296* (2013.01); *G16C 20/70* (2019.02)

(58) Field of Classification Search
CPC .. G01N 2201/1296; G01N 21/65; G06N 3/08; G06N 3/02; G16C 20/70
USPC ......................................................... 356/300
See application file for complete search history.

(56) References Cited

U.S. PATENT DOCUMENTS

| | | | | |
|---|---|---|---|---|
| 11,379,709 | B2 * | 7/2022 | Troy | G06N 3/084 |
| 11,428,638 | B2 * | 8/2022 | Xie | A61B 5/0075 |
| 2007/0155021 | A1 | 7/2007 | Zhang et al. | |
| 2010/0035243 | A1 | 2/2010 | Muller et al. | |
| 2015/0177152 | A1 | 6/2015 | Thomas et al. | |
| 2019/0250105 | A1 * | 8/2019 | Mahadevan-Jansen | G01J 3/44 |
| 2020/0003678 | A1 * | 1/2020 | Wolf | B82Y 40/00 |
| 2020/0284657 | A1 * | 9/2020 | Leblond | G01J 3/0227 |
| 2020/0300768 | A1 * | 9/2020 | Hikita | G06N 20/00 |
| 2020/0408789 | A1 * | 12/2020 | Kawamura | G06N 20/00 |
| 2021/0156784 | A1 * | 5/2021 | Hanashi | G01N 21/6458 |
| 2021/0248417 | A1 | 8/2021 | Taya et al. | |
| 2022/0101276 | A1 * | 3/2022 | Banatao | G16C 20/70 |
| 2022/0136971 | A1 * | 5/2022 | Bauer | G01N 33/4833 356/301 |
| 2022/0390351 | A1 * | 12/2022 | Saleh | G01N 15/1468 |

FOREIGN PATENT DOCUMENTS

| | | | | |
|---|---|---|---|---|
| JP | 2020-71166 A | 5/2020 | | |
| JP | 2020-101524 A | 7/2020 | | |
| TW | 202035972 A | * 10/2020 | ............ | G01N 21/27 |
| WO | 2007/044025 A2 | 4/2007 | | |
| WO | WO-2016139479 A1 | * 9/2016 | ............ | G01N 21/65 |
| WO | 2020/196074 A1 | 10/2020 | | |

OTHER PUBLICATIONS

Acquarelli et al., "Convolutional neural networks for vibrational spectroscopic data analysis", Analytica Chimica Acta, 2017, vol. 954, pp. 22-31 (10 pages total).

Liu et al., "Deep Convolutional Neural Networks for Raman Spec-trum Recognition: A Unified Solution", Analyst, Nov. 7, 2017, vol. 21, pp. 1-8 (8 pages total).

Fukuhara et al., "Feature visualization of Raman spectrum analysis with deep convolutional neural network", Analytica Chimica Acta, 2019, vol. 1087, pp. 11-19 (9 pages total).

Dojindo Laboratories, Catalog of "Protein cross-linkers and label-ing agents", Aug. 28, 2019, pp. 144-188, https://www.dojindo.co.jp/technical/catalog/08.pdf (49 pages total).

Weng et al., "Deep learning networks for the recognition and quantitation of surface-enhanced Raman spectroscopy", Analyst, 2020, vol. 145, pp. 4827-4835 (9 pages total).

Portela et al., "Highly sensitive SERS analysis of the cyclic Arg-Gly-Asp peptide ligands of cells using nanogap antennas", Journal of Biophotonics, 2017, vol. 10, No. 2, pp. 294-302 (9 pages total).

Huang et al., "SERS discrimination of single amino acid residue in single peptide by plasmonic nanocavities", Arxiv.org, Aug. 9, 2019, (22 pages total).

Extended European Search Report issued Jul. 27, 2022 in European Application No. 22160175.0.

Extended European Search Report issued Jul. 20, 2022 in European Application No. 22160173.5.

Communication issued Jun. 4, 2024 in European Application No. 22 160 173.5.

* cited by examiner

FIG. 17A

|  | Traning | Test |
|---|---|---|
| Ala | 3016 | 757 |
| Arg | 2653 | 666 |
| Asn | 3035 | 761 |
| Asp | 3106 | 779 |
| Cys | 4007 | 1004 |
| Gln | 2767 | 694 |
| Glu | 3095 | 776 |
| Gly | 3382 | 849 |
| His | 4054 | 1016 |
| Ile | 3609 | 904 |
| Leu | 3629 | 910 |
| Lys | 4216 | 1056 |
| Met | 3809 | 955 |
| Phe | 3087 | 774 |
| Pro | 3069 | 770 |
| Ser | 2643 | 664 |
| Thr | 2500 | 628 |
| Trp | 4567 | 1144 |
| Tyr | 4244 | 1064 |
| Val | 4071 | 1021 |
| NC | 3649 | 915 |

FIG. 17B

|  | Traning | Test |
|---|---|---|
| Ala | 2000 | 1000 |
| Arg | 2000 | 1000 |
| Asn | 2000 | 1000 |
| Asp | 2000 | 1000 |
| Cys | 2000 | 1000 |
| Gln | 2000 | 1000 |
| Glu | 2000 | 1000 |
| Gly | 2000 | 1000 |
| His | 2000 | 1000 |
| Ile | 2000 | 1000 |
| Leu | 2000 | 1000 |
| Lys | 2000 | 1000 |
| Met | 2000 | 1000 |
| Phe | 2000 | 1000 |
| Pro | 2000 | 1000 |
| Ser | 2000 | 1000 |
| Thr | 2000 | 1000 |
| Trp | 2000 | 1000 |
| Tyr | 2000 | 1000 |
| Val | 2000 | 1000 |
| NC | 4000 | 1000 |

FIG. 18A

| | Training | Test |
|---|---|---|
| FA | 1182 | 298 |
| FR | 1479 | 372 |
| FN | 1333 | 336 |
| FD | 1399 | 353 |
| FC | 1135 | 286 |
| FQ | 972 | 246 |
| FE | 1305 | 329 |
| FG | 1191 | 300 |
| FH | 1524 | 384 |
| FI | 1091 | 276 |
| FL | 1309 | 329 |
| FK | 1488 | 374 |
| FM | 1207 | 305 |
| FF | 1101 | 278 |
| FP | 1027 | 259 |
| FS | 1117 | 281 |
| FT | 1107 | 279 |
| FW | 1265 | 319 |
| FY | 1495 | 376 |
| FV | 1226 | 308 |
| AF | 1049 | 264 |
| RF | 700 | 177 |
| NF | 1053 | 265 |
| DF | 1320 | 333 |
| CF | 867 | 219 |
| QF | 934 | 236 |
| EF | 1072 | 270 |
| GF | 823 | 209 |
| HF | 1418 | 356 |
| IF | 1439 | 362 |
| LF | 1071 | 270 |
| KF | 886 | 225 |
| MF | 1189 | 300 |
| PF | 1119 | 283 |
| SF | 1370 | 345 |
| TF | 1024 | 259 |
| WF | 1442 | 363 |
| YF | 1213 | 305 |
| VF | 899 | 227 |
| NC | 854 | 216 |

FIG. 18B

| | Training | Test |
|---|---|---|
| FA | 700 | 350 |
| FR | 700 | 350 |
| FN | 700 | 350 |
| FD | 700 | 350 |
| FC | 700 | 350 |
| FQ | 700 | 350 |
| FE | 700 | 350 |
| FG | 700 | 350 |
| FH | 700 | 350 |
| FI | 700 | 350 |
| FL | 700 | 350 |
| FK | 700 | 350 |
| FM | 700 | 350 |
| FF | 700 | 350 |
| FP | 700 | 350 |
| FS | 700 | 350 |
| FT | 700 | 350 |
| FW | 700 | 350 |
| FY | 700 | 350 |
| FV | 700 | 350 |
| AF | 700 | 350 |
| RF | 700 | 350 |
| NF | 700 | 350 |
| DF | 700 | 350 |
| CF | 700 | 350 |
| QF | 700 | 350 |
| EF | 700 | 350 |
| GF | 700 | 350 |
| HF | 700 | 350 |
| IF | 700 | 350 |
| LF | 700 | 350 |
| KF | 700 | 350 |
| MF | 700 | 350 |
| PF | 700 | 350 |
| SF | 700 | 350 |
| TF | 700 | 350 |
| WF | 700 | 350 |
| YF | 700 | 350 |
| VF | 700 | 350 |
| NC | 700 | 350 |

FIG. 19A

|      | Training | Test |
|------|----------|------|
| AB38 | 8192     | 2905 |
| AB40 | 10124    | 2537 |
| AB42 | 11592    | 2905 |
| NC   | 3289     | 829  |

FIG. 19B

|      | Training | Test |
|------|----------|------|
| AB38 | 3000     | 1500 |
| AB40 | 3000     | 1500 |
| AB42 | 3000     | 1500 |
| NC   | 3000     | 1500 |

FIG. 19C

|      | Training | Test |
|------|----------|------|
| AB38 | 3000     | 1500 |
| AB40 | 3000     | 1500 |
| AB42 | 3000     | 1500 |
| NC   | 3000     | 1500 |

|      | AB38 | AB40 | AB42 | NC  | ACCURACY (%) |
|------|------|------|------|-----|--------------|
| AB38 | 1620 | 183  | 248  | 3   |              |
| AB40 | 42   | 2477 | 16   | 2   |              |
| AB42 | 86   | 37   | 2759 | 23  |              |
| NC   | 1    | 6    | 18   | 804 |              |

FIG. 24B

|      | AB38 | AB40 | AB42 | NC   | ACCURACY (%) |
|------|------|------|------|------|--------------|
| AB38 | 1500 | 0    | 0    | 0    | 100          |
| AB40 | 0    | 1500 | 0    | 0    | 100          |
| AB42 | 0    | 0    | 1500 | 0    | 100          |
| NC   | 0    | 0    | 0    | 1500 | 100          |

FIG. 24C

|      | AB38 | AB40 | AB42 | NC   | ACCURACY (%) |
|------|------|------|------|------|--------------|
| AB38 | 1452 | 14   | 98   | 1    |              |
| AB40 | 21   | 1484 | 5    | 1    |              |
| AB42 | 24   | 1    | 1385 | 3    |              |
| NC   | 3    | 1    | 12   | 1495 |              |

METHOD FOR ANALYZING TEST SUBSTANCE, ANALYZER, TRAINING METHOD, ANALYZER SYSTEM, AND ANALYSIS PROGRAM

CROSS REFERENCE TO RELATED APPLICATIONS

This application claims priority from prior Japanese Patent Application No. 2021-035597, filed on Mar. 5, 2021, entitled "METHOD FOR ANALYZING TEST SUBSTANCE, ANALYZER, TRAINING METHOD, ANALYZER SYSTEM, AND ANALYSIS PROGRAM", and prior Japanese Patent Application No. 2021-035593, filed on Mar. 5, 2021, entitled "METHOD FOR ANALYZING TEST SUBSTANCE, ANALYZER, TRAINING METHOD, ANALYZER SYSTEM, AND ANALYSIS PROGRAM", the entire contents of which are incorporated herein by reference.

FIELD OF THE INVENTION

The present invention relates to a method for analyzing a test substance contained in a measurement sample, an analyzer, a training method, an analyzer system, and an analysis program.

BACKGROUND

Japanese Laid-Open Patent Publication No. 2020-71166 discloses an apparatus for analyzing an object to be analyzed on the basis of a spectrum of light generated by the object to be analyzed that contains any one or more reference objects from among a plurality of reference objects, the apparatus including a processing unit, an input unit, a learning unit, and an analysis unit, in which the processing unit has a recurrent neural network (RNN). The input unit accepts entry of scalar data into each cell of the RNN. More specifically, assuming now that the spectrum of light measured with use of a spectrometer contains N data D(1) to D(N), where n-th data D(n) represents data of the n-th channel. n-Th cell among a plurality of cells connected in chain in an RNN model will be denoted as C(n). An input unit 20 inputs the optical spectra that contain N data D(1) to D(N), one by one into the RNN.

The optical spectra generated by the object to be analyzed may vary among the objects to be analyzed, even if originated from the same type of objects to be analyzed. The apparatus described in Japanese Laid-Open Patent Publication No. 2020-71166, designed to input the optical spectra one by one into the RNN, may yield different results output from the RNN depending on the input optical spectra, even if the optical spectra were originated from the same type of object to be analyzed, resulting in poor accuracy of analysis.

It is an object of the present invention to provide a method for analyzing a test substance contained in a measurement sample, an analyzer, a training method, an analyzer system, and an analysis program, proving high accuracy of analysis.

SUMMARY OF THE INVENTION

The scope of the present invention is defined solely by the appended claims, and is not affected to any degree by the statements within this summary.

The present invention relates to an analytical method for analyzing a test substance contained in a measurement sample, the method including: generating a data set based on a plurality of optical spectra acquired from a plurality of locations in the measurement sample; inputting the data set into a deep learning algorithm having a neural network structure; and outputting information on the test substance, on the basis of an analytical result from the deep learning algorithm. Since being designed to output information on a test substance, with use of a data set based on a plurality of optical spectra acquired from a plurality of locations in the measurement sample, the present invention can provide an analytical method that can analyze a test substance contained in the measurement sample with high accuracy of analysis.

The present invention relates to a training method for a deep learning algorithm for analyzing a test substance contained in a measurement sample, the training method includes: generating a data set based on a plurality of optical spectra acquired from a plurality of locations in the measurement sample that contains a known substance whose type, monomer sequence or a combination of atoms has been known; and inputting the data set into a deep learning algorithm having a neural network structure, together with label information that indicates the type, the monomer sequence or the combination of atoms of the known substance that corresponds to the data set. Since being designed to train a deep learning algorithm with use of a data set based on a plurality of optical spectra acquired from a plurality of locations in the measurement sample, the present invention can provide a deep learning algorithm that can analyze a test substance contained in the measurement sample with high accuracy of analysis.

The present invention relates to an analyzer (100, 100B) for analyzing a test substance contained in a measurement sample, the analyzer including a controller (10, 10B), in which the controller (10, 10B) is programmed to generate a data set based on a plurality of optical spectra acquired from a plurality of locations in the measurement sample, input the data set into a deep learning algorithm having a neural network structure, and output information on the test substance, on the basis of an analytical result from the deep learning algorithm. Since being designed to output information on the test substance with use of the data set based on the plurality of optical spectra acquired from the plurality of locations in the measurement sample, the present invention can provide an analyzer that can analyze a test substance contained in the measurement sample with high accuracy of analysis.

The present invention relates to an analyzer system (1) for analyzing a test substance contained in a measurement sample, the analyzer system including a detector (500) and an analyzer (100, 100B), in which the detector (500) includes a light source (520) and a photodetector (560), the analyzer (100, 100B) includes a controller (10, 10B), and the controller (10, 10B) is programmed to generate a data set based on a plurality of optical spectra acquired from a plurality of locations in the measurement sample, input the data set into a deep learning algorithm having a neural network structure, and output information on the test substance, on the basis of an analytical result from the deep learning algorithm. Since being designed to output information on the test substance with use of the data set based on the plurality of optical spectra acquired from the plurality of locations in the measurement sample, the present invention can provide an analyzer system that can analyze a test substance contained in the measurement sample with high accuracy of analysis.

The present invention relates to an analysis program (134) for a test substance contained in the measurement sample, when run on a computer, designed to execute processes of: generating a data set based on a plurality of optical spectra acquired from a plurality of locations in the measurement sample; inputting the data set into a deep learning algorithm having a neural network structure; and outputting information on the test substance, on the basis of an analytical result from the deep learning algorithm. Since being designed to output information on the test substance with use of the data set based on the plurality of optical spectra acquired from the plurality of locations in the measurement sample, the present invention can provide an analysis program that can analyze a test substance contained in the measurement sample with high accuracy of analysis.

According to the present invention, a test substance contained in a measurement sample may be detected with high accuracy of analysis.

BRIEF DESCRIPTION OF THE DRAWINGS

FIG. 17A shows the number of amino acid training data and the number of analytical performance evaluation data used in a prior method. FIG. 17B shows the number of amino acid training data and the number of analytical performance evaluation data used in Examples;

FIG. 18A shows the number of dipeptide training data and the number of analytical performance evaluation data used in a prior method. FIG. 18B shows the number of dipeptide training data and the number of analytical performance evaluation data used in Examples;

FIG. 19A shows the number of Aβ training data and the number of analytical performance evaluation data used in a prior method. FIG. 19B shows the number of Aβ training data and the number of analytical performance evaluation data, used in Example that used 100 spectra for generating an averaged spectral data. FIG. 19C shows the number of Aβ training data and the number of analytical performance evaluation data, used in Example that used three spectra for generating an averaged spectrum data;

FIG. 20 shows results of Comparative Example that used amino acids as the test substance;

FIG. 24A shows results of Comparative Example that used Aβ as the test substance. FIG. 24B shows results of Example in a case where 100 spectra were used to create the averaged spectral data set, and the test substance was Aβ. FIG. 24C shows results of Example in a case where three spectra were used to create the averaged spectral data set, and the test substance was A.

DETAILED DESCRIPTION OF THE PREFERRED EMBODIMENTS

Figure 1A:
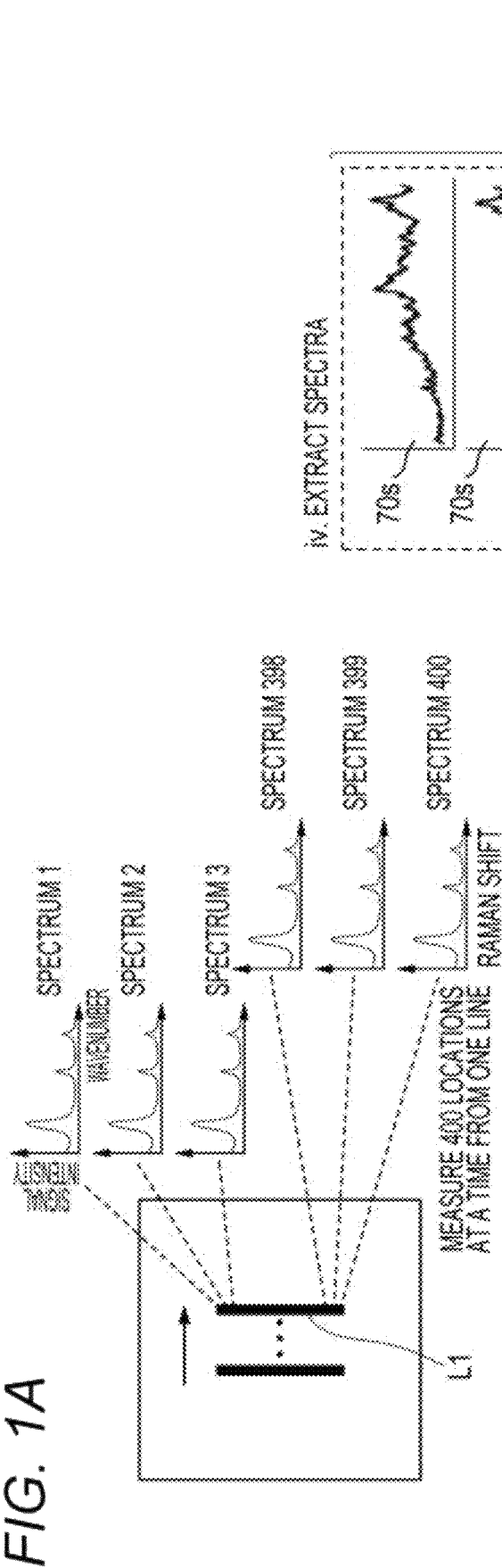
FIG. 1A is a view illustrating a method by which SERS spectra used for training a deep learning algorithm are acquired.

1. Outline of Method for Analyzing Test Substance

The method for analyzing a test substance contained in a measurement sample (also simply referred to as "analytical method", hereinafter) includes: generating a data set based on a plurality of optical spectra acquired from a plurality of locations in the measurement sample; inputting the data set into a deep learning algorithm having a neural network structure; and outputting information on the test substance, on the basis of an analytical result from the deep learning algorithm.

1-1. Acquisition of Measurement Sample and Optical Spectra

In the present embodiment, the test substance may contain at least one selected from the group consisting of amino acid, polypeptide, RNA, DNA, catecholamine, polyamine, and organic acid. The "polypeptide" is a compound in which two or more amino acids are linked by a peptide bond. The polypeptide is exemplified by dipeptide, oligopeptide, and protein. The test substance is contained in a solvent such as water or a buffer solution, or contained in a sample derived from a living body, such as blood, serum, plasma, saliva, ascites, pleural effusion, cerebrospinal fluid, lymph fluid, interstitial fluid, or urine.

The measurement sample is a sample subjected to optical detection of the test substance. The measurement sample is obtainable by contacting the test substance contained in the test sample, with other substance so as to be suited to the optical detection.

The optical detection method is not limited as long as the optical spectrum may be acquired. The optical spectrum is typically Raman spectrum, visible light absorption spectrum, ultraviolet absorption spectrum, fluorescence spectrum, near-infrared spectrum, or infrared spectrum. The Raman spectrum is typically surface enhanced Raman scattering (SERS) spectrum (referred to as SERS spectrum, hereinafter).

The SERS spectrum is acquired by irradiating a measurement sample that contains an aggregate of a metal nanoparticle bound to the test substance via a linker with excitation light.

An example of the measurement sample from which the SERS spectrum is acquired has been described in relation to a method of US 2007/0155021, according to which a metal nanoparticle and a linker are bound, a test substance is bound to a complex of the metal nanoparticle and the linker, and the metal nanoparticle having the test substance bound thereto is aggregated.

The measurement sample from which the optical spectrum is acquired may be prepared by placing the sample in a liquid state on a base, followed by drying. The base employable here is exemplified by glass base such as cover glass, slide glass, or glass-bottomed plate.

The measurement sample from which the optical spectrum is acquired may also be a sample in a liquid state contained in a transparent vial.

The optical spectrum may be acquired by causing flow of a measurement sample in a liquid state through a channel, and irradiating the measurement sample that flows through the channel with excitation light.

The optical spectrum may be acquired by irradiating the measurement sample with light, and detecting scattered light, transmitted light, reflected light, fluorescence, or the like emitted from the test substance or the substance bound to the test substance, with use of a detector. The scattered light may be a scattered light (Raman scattered light) whose wavelength is different from a predetermined wavelength of the light incident on the measurement sample.

1-2. Training of Deep Learning Algorithm

For the analytical method, a deep learning algorithm trained by training data set 72 is used. The training method for a deep learning algorithm includes: generating a data set based on a plurality of optical spectra acquired from a plurality of locations in the measurement sample that contains a known substance whose type, monomer sequence or a combination of atoms has been known; and inputting the data set into a deep learning algorithm having a neural network structure, together with label information that indicates the type, the monomer sequence or the combination of atoms of the known substance that corresponds to the data set. The known substance may contain at least one selected from the group consisting of amino acid, polypeptide, RNA, DNA, catecholamine, polyamine, and organic acid, similarly to the test substance. The combination of atoms that constitute the known substance is typically a structure or functional group in a molecule that constitutes the known substance, and is exemplified by those causing C—H stretching, O—H stretching, or $CH_2$ symmetric stretching.

(1) Creation of Training Data Set

A method for acquiring a training data set will be explained with reference to FIG. 1. Although FIG. 1 illustrates a method with use of SERS spectrum, the training data set may be acquired by a similar method with use of an optical spectrum other than the SERS spectrum. FIG. 1A illustrates a method for obtaining SERS spectra with use of a slit-scanning confocal Raman microscope. The slit scanning confocal Raman microscope employable here may be a laser Raman microscope RAMANtouch/RAMANforce (Nanophoton Corporation), for example. This microscope can irradiate the measurement sample with a line beam, denoted by a reference sign L1, of laser light as excitation light. This microscope can acquire 400 SERS spectra, from a single line beam of excitation light L1. Each of Spectrum 1 to Spectrum 400 indicates a SERS spectrum acquired from a single line beam of excitation light L1, with the abscissa denoting wavenumber, and the ordinate denoting signal intensity of light at each wavenumber.

Figure 1B:
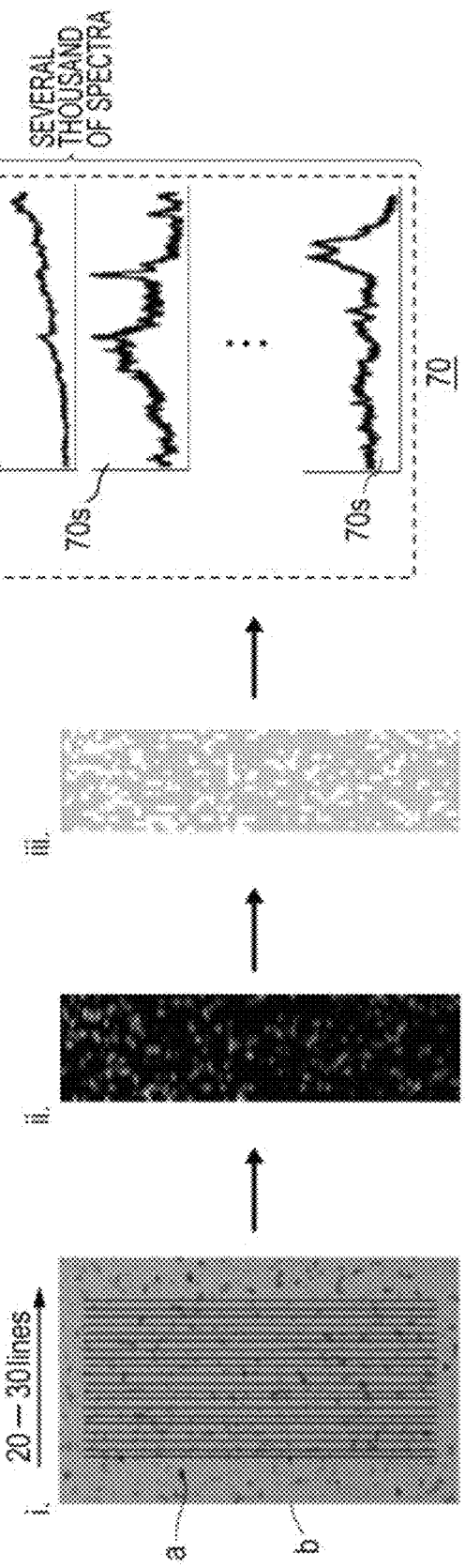
FIG. 1B is a view illustrating a method by which a plurality of SERS spectra are acquired from a plurality of locations in a measurement sample that contains a known substance.

FIG. 1B illustrates a method for acquiring a plurality of SERS spectra 70 from a plurality of locations in a measurement sample that contains a known substance. An image presented for step i represents a bright field image of the measurement sample on the slide glass "b", overlaid with lines that indicate locations irradiated with the line beam of the excitation light. Reference sign "a" denotes an aggregate of metal nanoparticles. In step i, the measurement sample is irradiated with the line beam of excitation light to acquire 400 SERS spectra as described previously referring to FIG. 1A. Different locations are irradiated with approximately 20 to 30 line beams of the excitation light, and 400 SERS spectra are acquired on each occasion.

From steps ii to iv, SERS spectra 70s, having SERS equal to or larger than a threshold value appear therein, are selected from the plurality of SERS spectra having been obtained in step i. Hence, the SERS spectrum 70 that corresponds to SERS generated from the aggregate of the metal nanoparticles may be selected. First, in step ii, pixels that correspond to the locations irradiated with the excitation light are selected on the image presented for step i, and combined. In the image presented for step ii, the darker the area, the weaker the SERS (i.e., optical signal), meanwhile the brighter the area, the stronger the SERS. The image presented for step ii indicates SERS signal intensity in gradation levels typically from 0 to 255. The images presented for steps i and ii may be created typically from SERS signal intensity in a fingerprint area, or from the SERS signal intensity in a silent area. The images presented for steps i and ii may be created by calculation from the SERS signal intensity in a plurality of wavenumber bands, or from the SERS signal intensity in a single wavenumber band. Next in step iii, the individual pixels selected in step ii are binarized on the basis of the SERS signal intensity. An operator may take part in binarization while setting a threshold value. The binarization may rely upon processing such as discriminant analysis, dynamic threshold method, percentile method, mode method, Laplacian histogram method, differential histogram method, and level slicing.

The wavenumber band is given by a predetermined wavenumber, or given by a wavenumber region with a predetermined range obtainable by dividing the entire wavenumber region. The signal intensity of the optical spectrum (SERS in this embodiment) in the wavenumber band means, if the wavenumber band being given by a predetermined wavenumber, the SERS signal intensity at that wavenumber, meanwhile, if the wavenumber band being a wavenumber region with a predetermined range, a representative value of the SERS signal intensity in that wavenumber band (for example, maximum value, average value, or centroid value, for example).

In the image presented for step iii, pixels with the SERS signal intensity equal to or larger than the threshold value are depicted as blank, meanwhile the pixels with the SERS signal intensity smaller than the threshold value are depicted in gray.

In step iv, the SERS spectrum 70s of the individual pixels, whose SERS signal intensities having been judged to be equal to or larger than the threshold value in step iii, are selected. The SERS spectra 70s acquired in step iv may be subjected to processes such as baseline correction, scatter correction, denoising, scaling, and principal component analysis as necessary.

In the example illustrated in FIG. 1B, optical spectra are acquired from a plurality of locations in the measurement sample, by changing position of irradiation with the excitation light relative to the measurement sample on the slide. Meanwhile, in a case where the optical spectrum is acquired by irradiating the measurement sample contained in a transparent vial with the excitation light, the optical spectra may be acquired from a plurality of locations in the measurement sample, without changing the position of irradiation with the excitation light. This is because the test substance in the measurement sample, under irradiation with the excitation light, can vary the position due to Brownian motion. Alternatively in a case where the optical spectra are acquired from the measurement sample that flows through a flow channel, the optical spectra are obtainable from a plurality of locations in the measurement sample, since position of irradiation with the excitation light varies as the measurement sample flows.

The excitation light may be irradiated in the form of beam spot, although FIG. 1 illustrates an exemplary case with use of the excitation light in the form of line beam.

Figure 2:
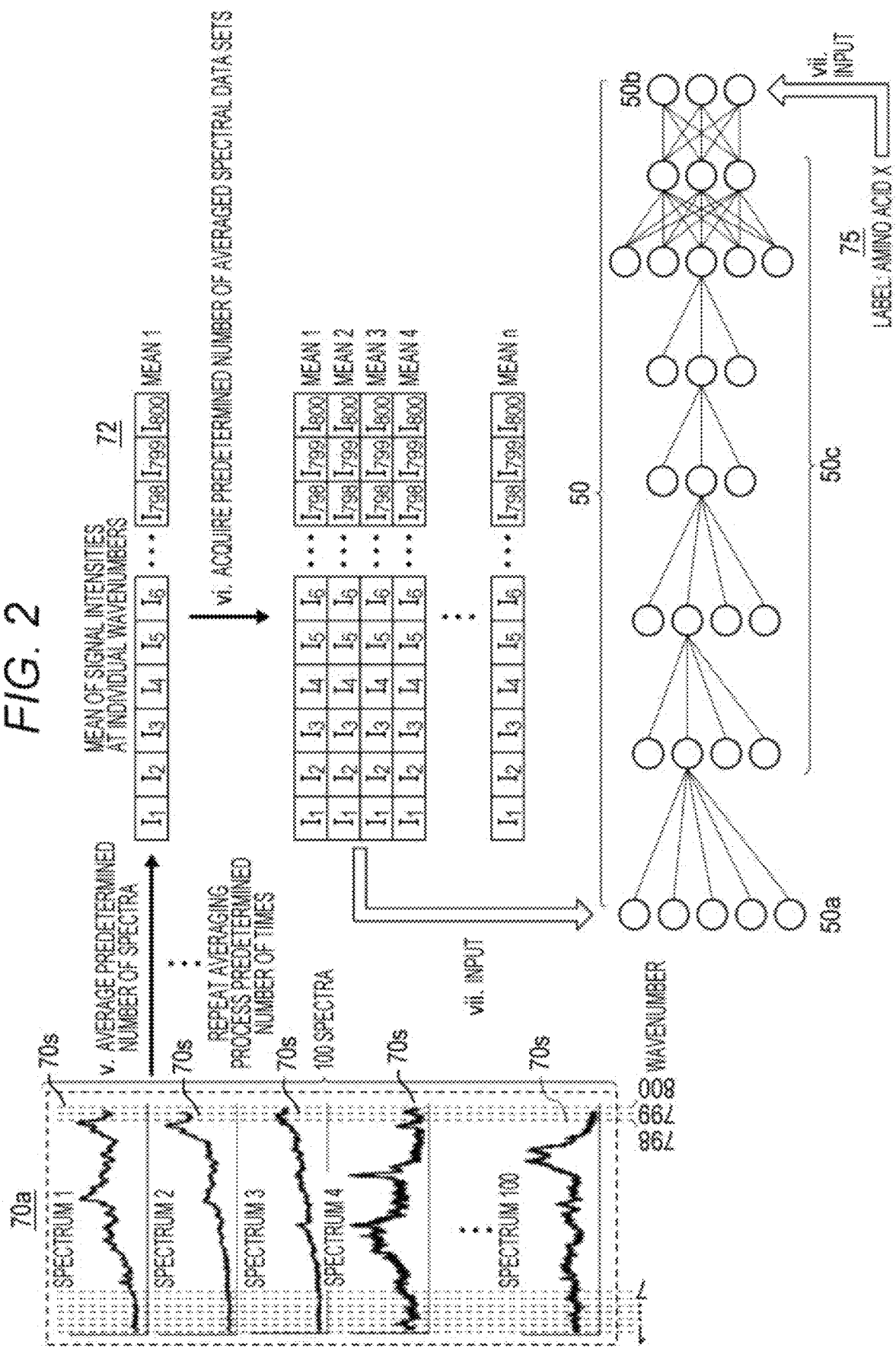
FIG. 2 is a view illustrating a method by which a training data set 72 is acquired, and a deep learning algorithm is trained.

In step v illustrated in FIG. 2, a predetermined number of SERS spectra are randomly extracted from the SERS spectrum 70 obtained in step iv, and then averaged. SERS spectrum 70a represents a predetermined number (100, in this case) of extracted SERS spectra. The SERS spectrum 70a that contains the extracted predetermined number of SERS spectra 70s is also referred to as a "subset" in this specification. The number of SERS spectra 70s contained in one subset may only be plural, and is preferably at least three. The upper limit of the number of SERS spectra 70s contained in one subset is not limited, as long as the SERS spectra 70s are extractable from the SERS spectrum 70.

The signal intensities of the SERS spectra contained in the subset are averaged for each identical wavenumber band. Referring now to FIG. 2, in an exemplary case where the SERS spectrum 70a contains spectrum 1, spectrum 2, and so on up to spectrum 100, and where each SERS spectrum covers a wavenumber range from the first band up to 800th band, an average value $I_1$ of the signal intensity in the first wavenumber band is calculated by adding the signal intensity in the first wavenumber band of spectrum 1, the signal intensity in the first wavenumber band of spectrum 2, the signal intensity in the first wavenumber band of spectrum 3, and the signal intensity in the first wavenumber band of spectrum 4, and so on up to the signal intensity in the first wavenumber band of spectrum 100, and then by dividing the sum by the total number of the SERS spectra (100, in this case). For the signal intensities in the second and subsequent wavenumber bands, the arithmetic means $I_2$, $I_3$, $I_4$, $I_5$, and so on are similarly calculated. This process is repeated from the first wavenumber band to the 800th wavenumber band, to calculate arithmetic means $I_1$ to $I_{800}$. A data set of the calculated average values $I_1$ to $I_{800}$ is defined to be an averaged spectral data set 72 of the first subset (mean 1). Step v and step vi are repeated a predetermined number of times, to obtain an averaged spectral data set 72 of the second subset (mean 2), an averaged spectral data set 72 of the third subset (mean 3), and so on up to an averaged spectral data set 72 of the n-th subset (mean n). The averaged spectral data set 72 is an example of a training data set.

The signal intensities of the optical spectrum (SERS, in this embodiment) in the same wavenumber band are preferably the signal intensities in the same wavenumber band, when viewed among the plurality of SERS spectra 70 as illustrated in FIG. 2, but are not limited as long as the signal intensities are in a substantially same wavenumber band.

(2) Training of Deep Learning Algorithm

In step vii, the averaged spectral data set 72, and a second training data which is label information that indicates the type or the monomer sequence of the known substance contained in the measurement sample on the slide glass b, are input into a deep learning algorithm 50. The label information may be a name of the known substance, a monomer sequence name of the known substance, abbreviations representing them, label value, or the like.

More specifically in step vii, the averaged spectral data set 72 (mean 1) is input into an input layer 50a of the deep learning algorithm 50, and the label information 75 is input into an output layer 50b. In FIG. 2, "amino acid X" is input as the label information 75. Reference sign 50c denotes an intermediate layer of the deep learning algorithm 50. In response to entry of the averaged spectral data set 72 and the label information 75, weight which corresponds to connection strength of the individual layers in the deep learning algorithm 50 is updated.

Also for each of the averaged spectral data set 72 (mean 2) and subsequent data sets, each of the averaged spectral data set 72 (mean 2) and so on is input into the input layer 50a, the label information 75 is input into the output layer 50b, and the weight is updated in a similar manner. Steps i to vii are optionally repeated also for any other measurement sample that contains the same kind of test substance. A learned deep learning algorithm (referred to as a deep learning algorithm 60, hereinafter) is thus created.

As described previously, the averaged spectral data set 72 is generated on the basis of the plurality of optical spectra (SERS spectrum 70, in this embodiment) acquired from a plurality of locations (400 locations per a single line beam of the excitation light L1) of the measurement sample on the slide glass b. This enables absorption of any variation if occurred in every SERS spectrum, and creation of the deep learning algorithm 60 that can output a highly accurate analytical result.

The deep learning algorithm 50 is not limited as long as it has a neural network structure. For example, the deep learning algorithm 50 contains a convolutional neural network, a full-connected neural network, or a combination of them. The deep learning algorithm 50 may be an absolutely untrained algorithm or an already-trained algorithm.

The data that constitutes the averaged spectral data set 72 may alternatively be integrated value, multiplied value, or divided value, in place of the arithmetic mean. The integrated value is given by integrating the signal intensities in the same wavenumber band of the individual SERS spectra in the SERS spectrum 70a. The multiplied value is given by adding up the signal intensities in the same wavenumber band of the individual SERS spectra in the SERS spectrum 70a, meanwhile the divided value is given by dividing the signal intensities in the same wavenumber band of the individual SERS spectra in the SERS spectrum 70a according to a predetermined order.

1-3. Generation of Data Set for Analysis, and Analytical Method

Figure 3:
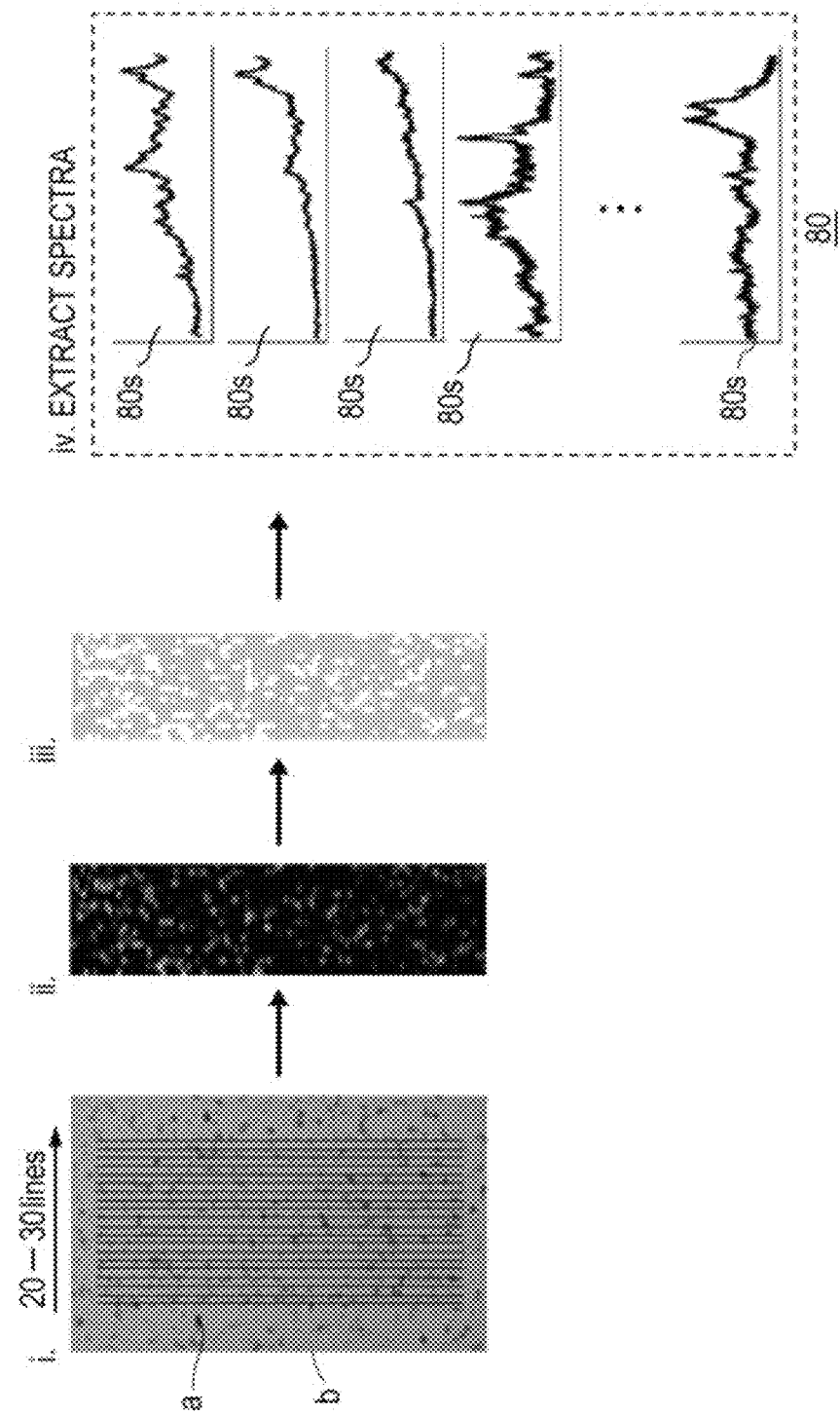
FIG. 3 is a view illustrating a method by which SERS spectra are acquired from a measurement sample to be analyzed.
Figure 4:
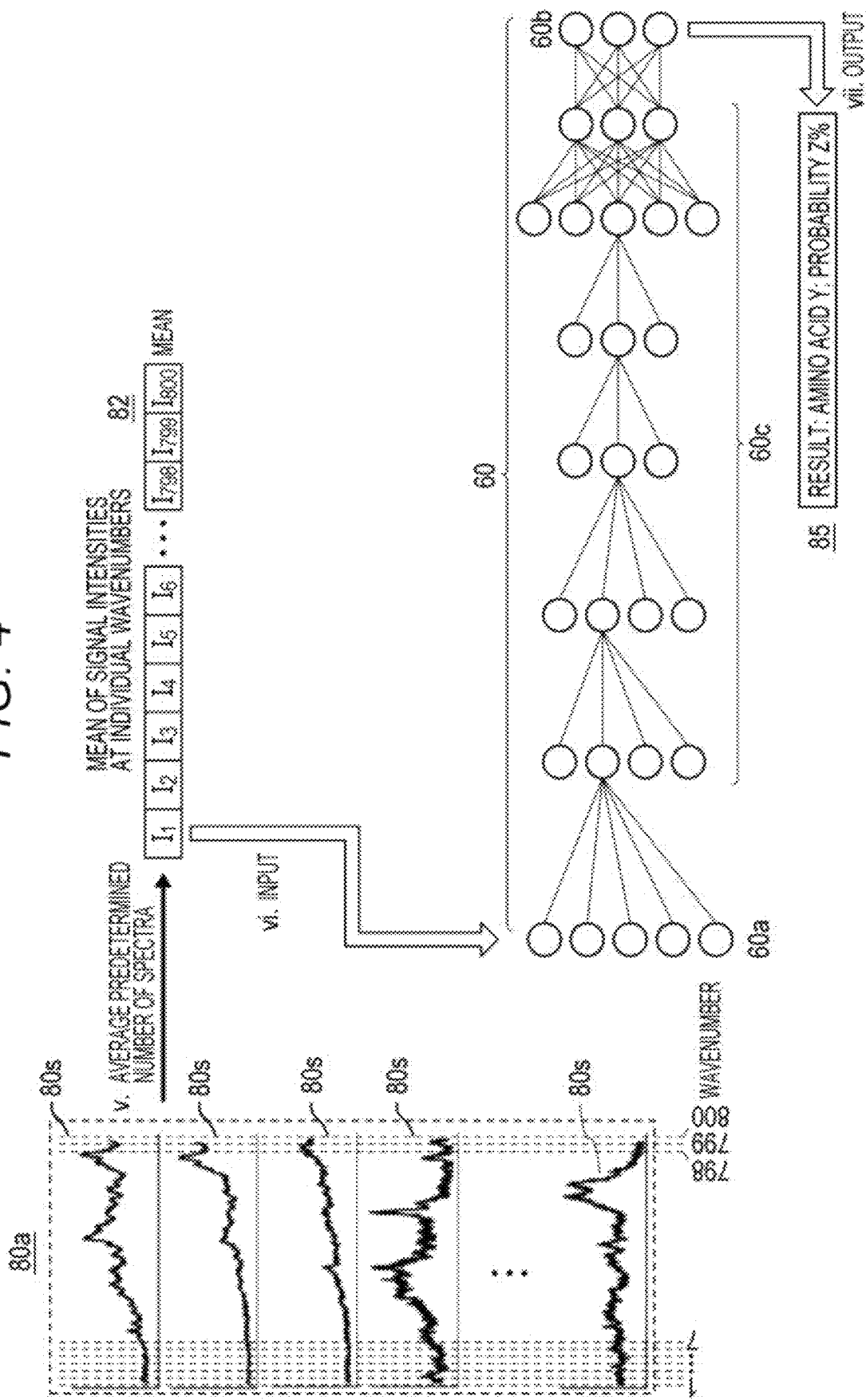
FIG. 4 is a view illustrating a method by which a data set 82 for analysis is acquired and input into a deep learning algorithm.

Generation of a data set for analysis to be input into the deep learning algorithm 60, and output of information on a test substance based on an analytical result from the deep learning algorithm 60 will be explained, with reference to FIGS. 3 and 4.

The data set for analysis is generated in the same manner as steps i to v for generating the averaged spectral data set 72, previously illustrated in section 1-2. (1), and in FIGS. 1 and 2. More specifically, first in step i illustrated in FIG. 3, the measurement sample to be analyzed is irradiated with twenty to thirty line beams of the excitation light, to acquire SERS spectra. Next, steps ii to iv are carried out to select SERS spectra 80s having SERS equal to or larger than a threshold value, from among the plurality of SERS spectra acquired in step i. A method for selecting SERS spectra 80s with SERS equal to or larger than a threshold value is incorporated herein from the explanation above in steps ii to iv in section 1-2. (1). This enables, in step iv, selection of the SERS spectra 80, which are SERS spectra ascribed to the aggregated metal nanoparticles. In step v illustrated in FIG. 4, a predetermined number (100 in this example) of SERS spectra 80a are randomly extracted from the SERS spectra 80 having been acquired in step iv, and an averaged spectral data set 82 of the thus extracted predetermined number of SERS spectra 80a is obtained as a data set for analysis. A method for averaging the data set 80a of the predetermined number of optical spectra is incorporated herein from the explanation above in step v in section 1-2. (1). In step vi, the averaged spectral data set 82 is input into an input layer 60a of the learned deep learning algorithm 60. In step vii, the deep learning algorithm 60 outputs an analytical result 85 from an output layer 60c. In an exemplary case illustrated in FIG. 3, the analytical result 85 contains "amino acid Y" as the type of the known substance, and a probability thereof. As in this case, the analytical result 85 may contain a label that indicates the type of the known substance predicted for the test substance, and a probability that the test substance matches the predicted known substance. The analytical result 85 may alternatively contain a label that indicates the monomer sequence of the known substance predicted for the test substance, and the probability that the test substance matches the predicted known substance. The analytical result 85 may still alternatively contain a combination of atoms that constitute the known substance predicted for the test substance, and the probability that the test substance matches the predicted known substance. The combination of atoms that constitute the known substance is typically a structure or functional group in a molecule that constitutes the known substance, and is exemplified by those causing C—H stretching, O—H stretching, or CH2 symmetric stretching.

The analytical result 85 may contain information on types of a plurality of predicted known substances and/or monomer sequences of a plurality of predicted known substances, for a single test substance. In a case where the probability that the test substance matches a predicted known substance is low, the analytical result 85 may contain information such as "unknown substance" or "analysis not possible".

As described previously, the averaged spectral data set 82 is generated on the basis of the plurality of optical spectra (SERS spectrum 80, in this embodiment) acquired from a plurality of locations (in this embodiment, 400 locations per a single line beam of the excitation light L1) of the measurement sample on the slide glass b. This enables absorption of any variation if occurred in every SERS spectrum, and output of a highly accurate analytical result from the deep learning algorithm 60.

Although having described the method for generating the averaged spectral data set 82 as the data set for analysis, the method may employ integrated value, multiplied value, or divided value in place of the arithmetic mean, likewise the training data set.

Although having described an exemplary case where the optical spectrum is the SERS spectrum, any optical spectrum other than the SERS spectrum is employable. Although having described an exemplary case where the optical spectrum was presented with the wavenumber plotted on the abscissa, wavelength may alternatively be plotted on the abscissa.

The measurement sample used for acquiring the training data set and the measurement sample for acquiring the data set for analysis are preferably prepared by the same method. In a case where a liquid measurement sample was used in the acquisition of the training data set, use of a liquid measurement sample is preferred also in the acquisition of the data set for analysis. Similarly, in a case where a dried measurement sample was used in acquisition of the training data set, use of a dried measurement sample is preferred also in the acquisition of the data set for analysis.

2. Analyzer System for Test Substance

Figure 5:
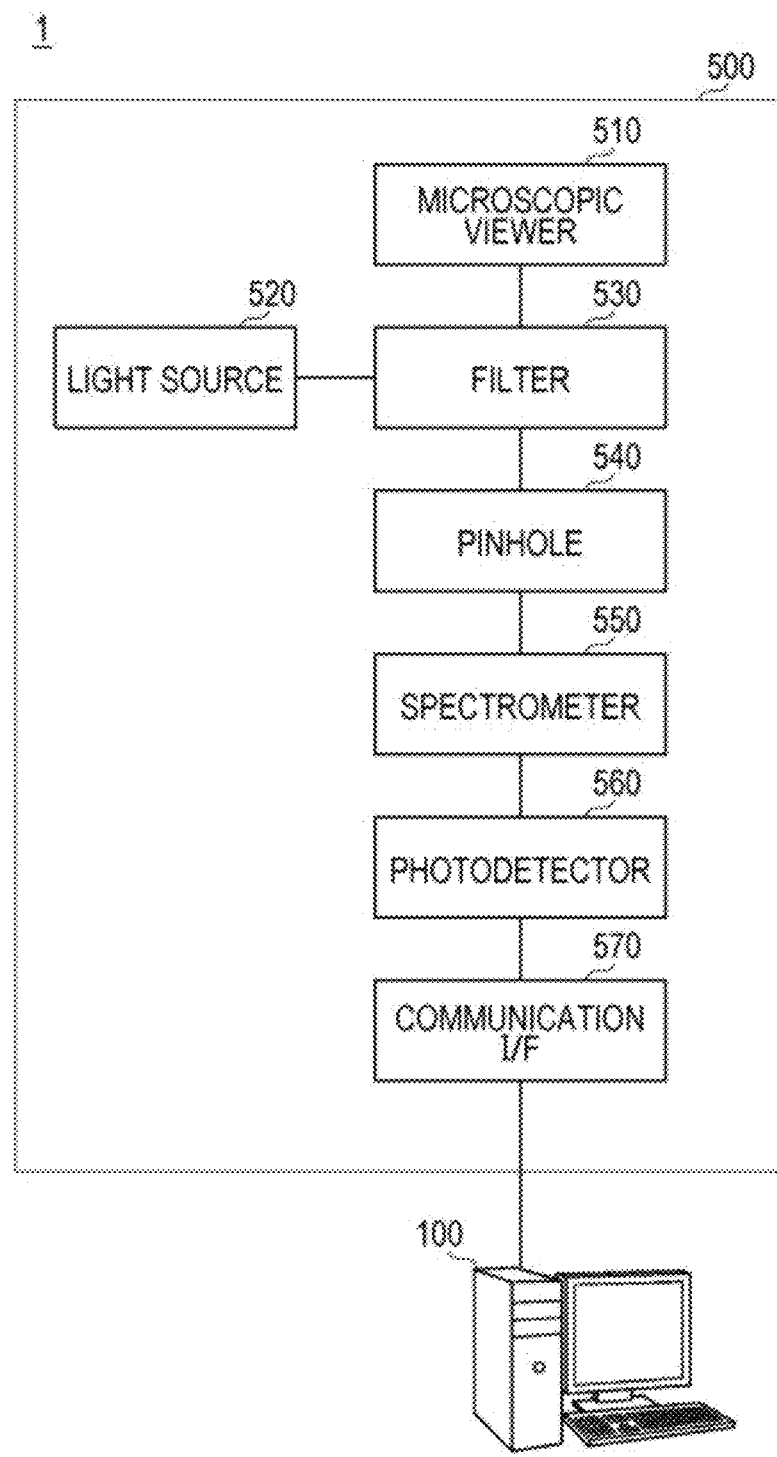
FIG. 5 is a view illustrating a configuration of an analyzer system 1.

An analyzer system 1 for analyzing a test substance contained in a measurement sample (also simply referred to as "analyzer system 1", hereinafter) will be explained. FIG. 5 illustrates an outline of the analyzer system 1. The analyzer system 1 includes a detector 500 that acquires optical spectra, and an analyzer 100 that trains the deep learning algorithm 50 and outputs information on the test substance with use of the trained deep learning algorithm 60.

2-1. Detector 500

Figure 6A:
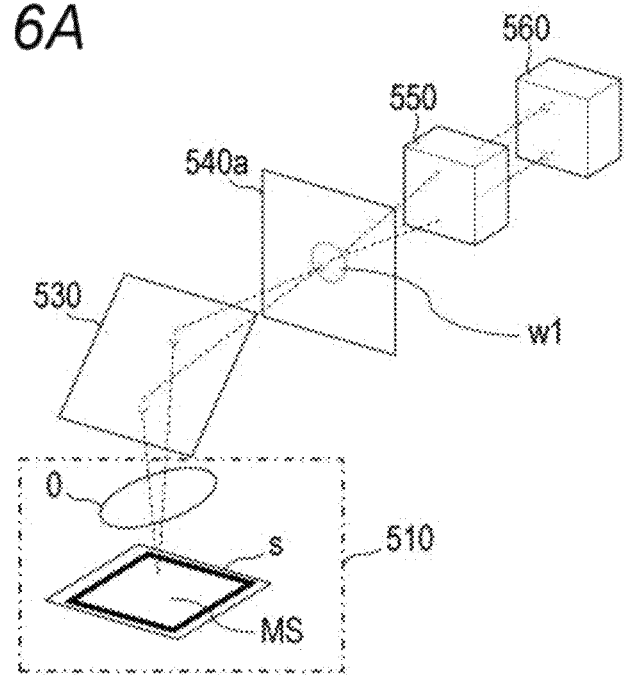
FIG. 6A is a view illustrating an exemplary hardware configuration of a detector 500.
Figure 6B:
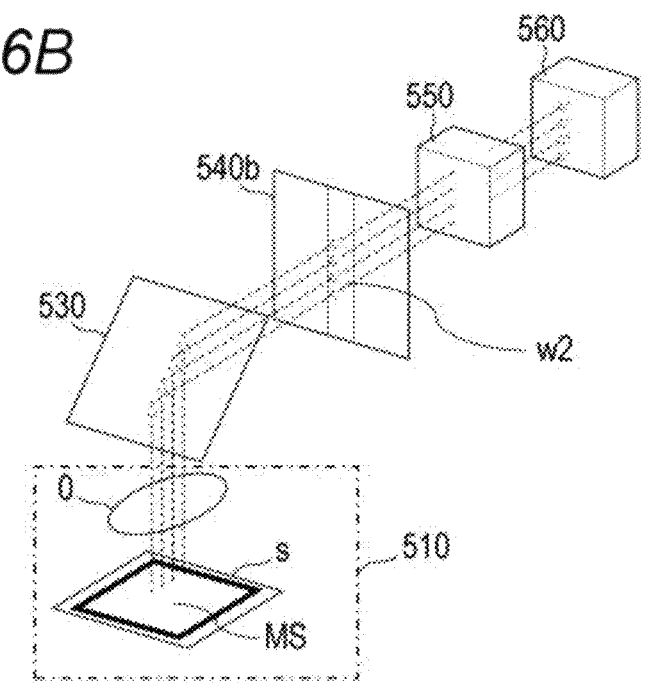
FIG. 6B is a view illustrating another exemplary hardware configuration of the detector 500.

A structure of the detector 500 will be described with reference to FIGS. 5 and 6. The detector 500 includes a microscopic viewer 510 that magnifies an image of the measurement sample placed thereon, a light source 520 that emits light with which the measurement sample is irradiated (irradiation light), a filter 530 that separates optical paths of the light emitted from the light source 520 and the light (return light) emitted from the measurement sample, a pinhole 540 that narrows the optical path of the return light, a spectrometer 550 that disperses the return light to a predetermined wavelength, a photodetector 560 that receives the return light, and a communication interface 570. The light source 520 is preferably a laser light source. Type of the laser light source is selectable depending on the wavelength of the irradiation light with which the measurement sample is irradiated. The filter 530 is a dichroic filter. The pinhole 540, employed in a case where the measurement sample is irradiated with the irradiation light in the form of beam spot, is a pinhole 540a having a circular optical path window w1 as illustrated in FIG. 6A. On the other hand, a pinhole 540b having a slit-shaped optical path window w2 illustrated in FIG. 6B is employable, in a case where the measurement sample is irradiated with the irradiation light in the form of line beam. The photodetector 560 is typically a CCD camera. The photodetector 560 is communicably connected to the analyzer 100 via the communication interface 570. The communication interface 570 is typically a USB interface. As illustrated in FIGS. 6A and 6B, the microscopic viewer 510 includes an objective lens O and a stage S on which a measurement sample MS is placed. In FIG. 6, a broken line indicates an optical path of the return light. The detector 500 is exemplified by a laser Raman microscope RAMANtouch/RAMANforce (Nanophoton Corporation), and a multi-focus Raman microscope.

Detection conditions in a case where the optical spectrum is the SRES spectrum obtained with use of metal nanoparticles are as follows.

Excitation wavelength: 660 nm
Excitation intensity: 2.5 mW/$\mu$m$^2$
Exposure time: 0.5 sec/line
Objective lens: 40×, NA=1.25

The conditions may be properly set depending on the type of the test substance, material of the metal nanoparticle, and shape of the metal nanoparticle.

2-2. Analyzer 100

(1) Hardware Configuration

Figure 7:
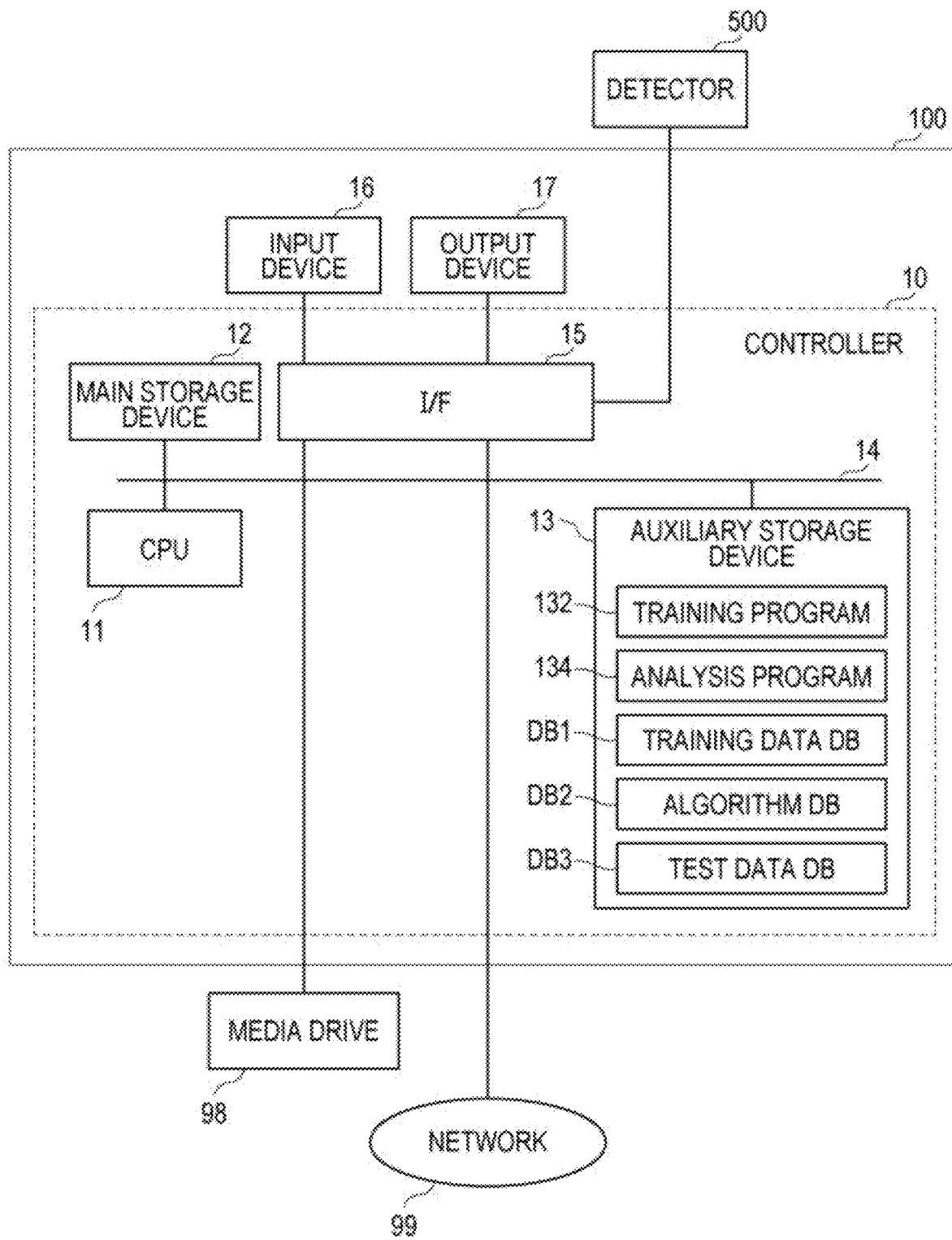
FIG. 7 is a view illustrating the analyzer system 1 and peripheral devices thereof, for explaining a hardware configuration of an analyzer 100.

FIG. 7 illustrates a hardware configuration of the analyzer 100. The analyzer 100 is typically constituted by a general-purpose computer, trains the deep learning algorithm 50 with use of a training program 132, and outputs information on the test substance with use of an analysis program 134 and the trained deep learning algorithm 60.

The analyzer 100 is connected to the detector 500. The analyzer 100 includes a controller 10, an input device 16, and an output device 17. The analyzer 100 is connected to a media drive 98 and a network 99.

The controller 10 includes a central processing unit (CPU) 11 that processes data, a main storage device 12 used as a work area for data processing, an auxiliary storage device 13, a bus 14 that transmits data among the individual units, and an interface (I/F) 15 through which data is input or output to or from an external device. The input device 16 and the output device 17 are connected to an interface (I/F) 15. The input device 16 is a keyboard, a mouse, or the like, and the output device 17 is a liquid crystal display, an organic EL display, or the like. The auxiliary storage device 13 is a solid state drive, a hard disk drive, or the like. The auxiliary storage device 13 stores a training program 132, an analysis program 134, a training data database (DB) DB1 that stores a training data set and data necessary for generating the data set, an algorithm database (DB) DB2 that stores an algorithm, and a test data database (DB) DB3 that stores a data set for analysis (averaged spectral data set 82) and data necessary for generating the data. With use of the training program 132, the analyzer 100 executes a training process of the deep learning algorithm. With use of the analysis program 134, the analyzer 100 executes an analysis process of the measurement sample. The training data database DB1 stores the plurality of optical spectra 70 acquired from the measurement sample that contains a known substance, the averaged spectral data set 72, and the label information 75. The algorithm database DB2 stores the untrained deep learning algorithm 50 and/or the trained deep learning algorithm 60.

(2) Functional Configuration

Figure 8:
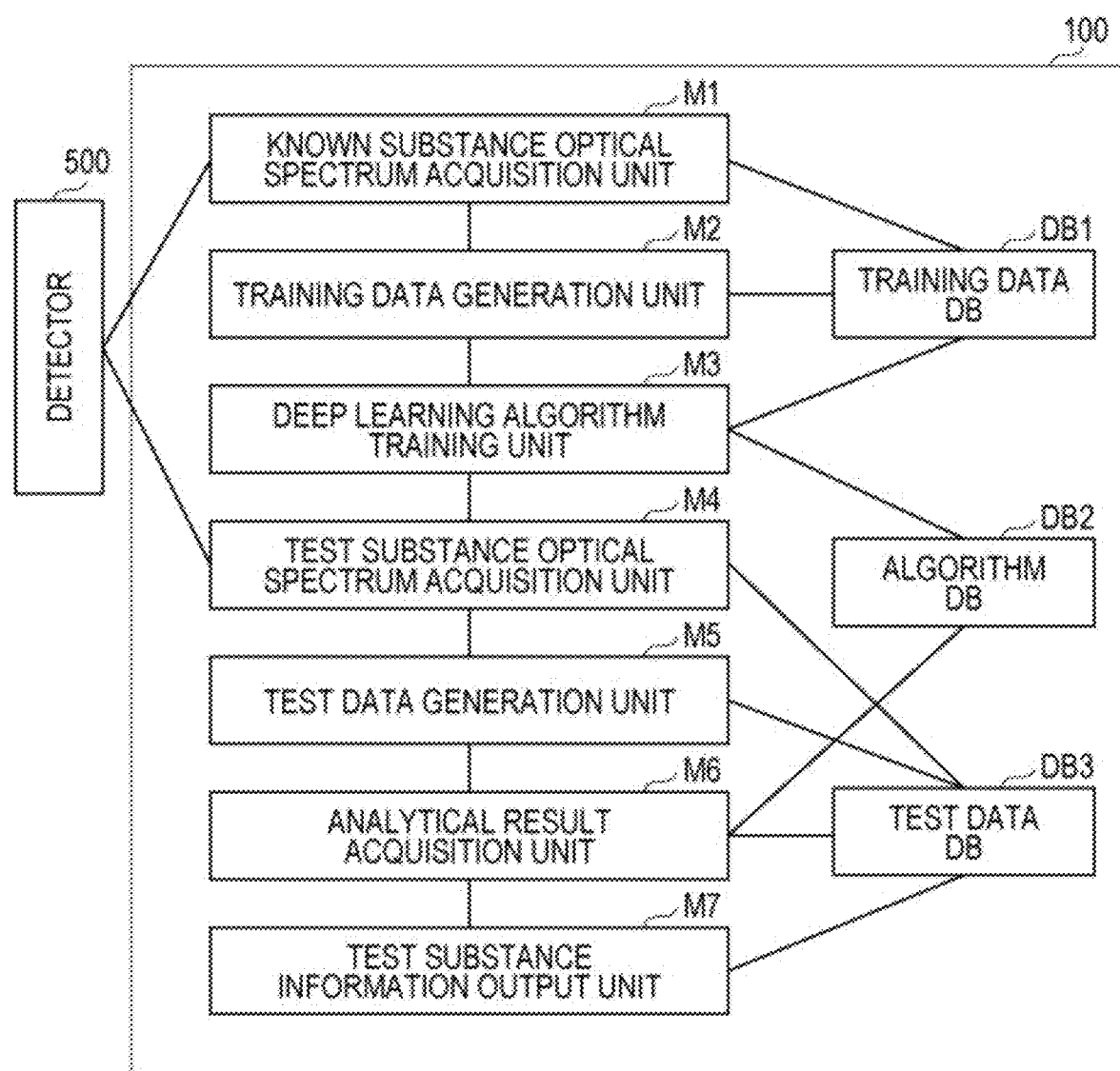
FIG. 8 is a view illustrating the analyzer system 1, for explaining a functional configuration of the analyzer 100.

FIG. 8 illustrates a functional configuration diagram of the analyzer 100.

The analyzer 100 includes a known substance optical spectrum acquisition unit M1, a training data generation unit M2, a deep learning algorithm training unit M3, a test substance optical spectrum acquisition unit M4, a test data generation unit M5, an analytical result acquisition unit M6, a test substance information output unit M7, the training data database DB1, the algorithm database DB2, and the test data database DB3.

Figure 9:
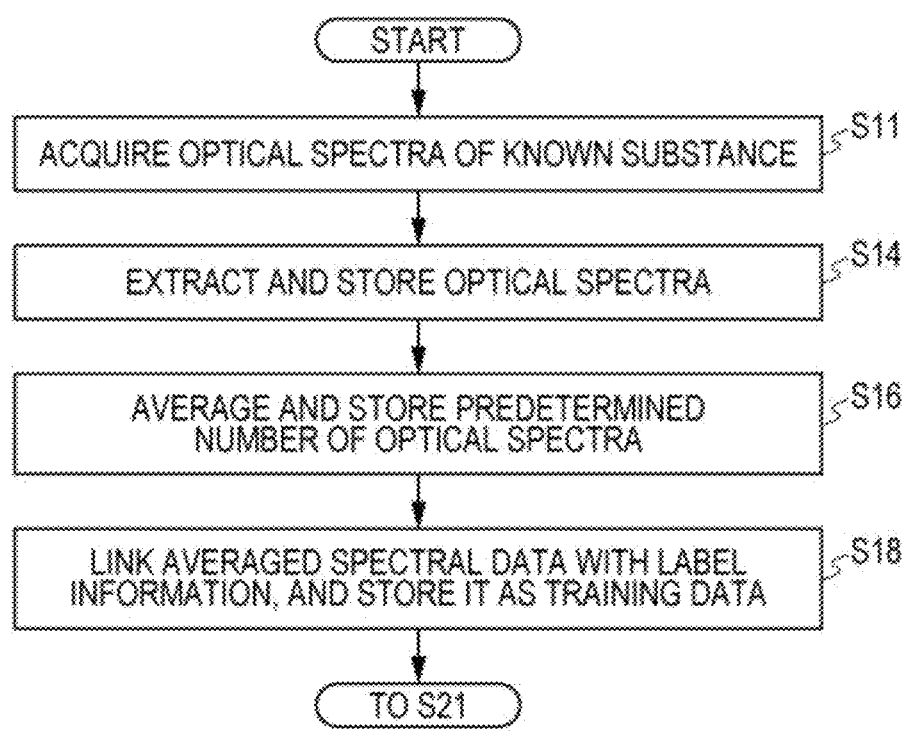
FIG. 9 is a view illustrating a process flow of a first process of a training program 132.

The known substance optical spectrum acquisition unit M1 corresponds to step S11 illustrated in FIG. 9. The training data generation unit M2 corresponds to steps S14 to S18 illustrated in FIG. 9. The deep learning algorithm training unit M3 corresponds to steps S21 to S24 illustrated in FIG. 10. The test substance optical spectrum acquisition unit M4 corresponds to step S31 illustrated in FIG. 11. The test data generation unit M5 corresponds to steps S34 to S36 illustrated in FIG. 11. The analytical result acquisition unit M6 corresponds to steps S41 to S43 illustrated in FIG. 12. The test substance information output unit M7 corresponds to step S44 illustrated in FIG. 12.

2-3. Processes of Training Program 132

Figure 10:
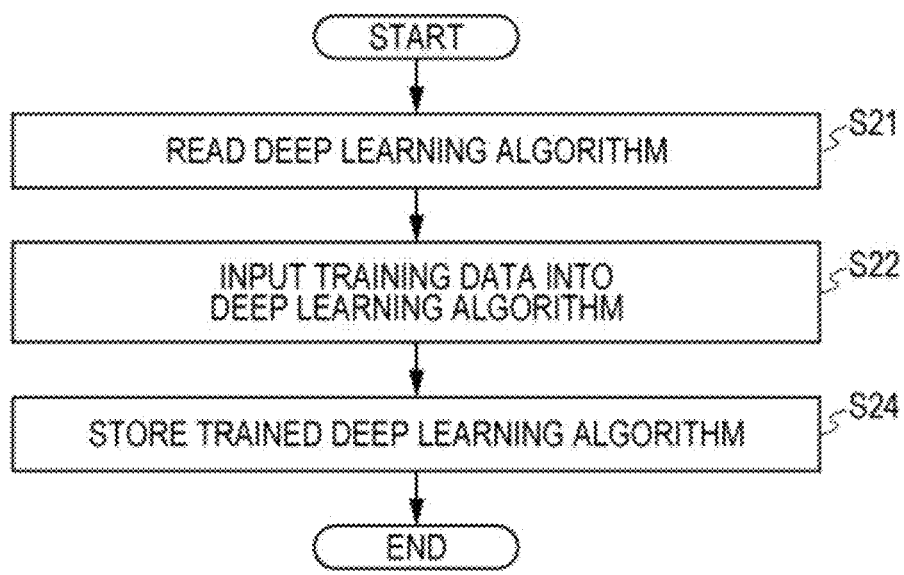
FIG. 10 is a view illustrating a process flow of a second process of the training program 132.

FIGS. 9 and 10 illustrate flows of the training process of the deep learning algorithm executed by the controller 10 according to the training program 132.

The controller 10 accepts a process start command input through the input device 16 by an operator, and acquires a plurality of optical spectra of a known substance in step S11 illustrated in FIG. 9. More specifically, the controller 10 receives, from the detector 500, data that represents an optical spectrum detected by the photodetector 560 when the measurement sample that contains a known substance is irradiated with the irradiation light (excitation light). In a case where the data that represents the optical spectrum is stored in the training data database DB1, the controller 10 acquires the optical spectrum of the known substance by reading the data from the training data database DB1.

In step S14, the controller 10 extracts optical spectra ascribed to the test substance or a substance bound to the test substance, from the plurality of optical spectra acquired in step S11. The optical spectra ascribed to the test substance or the substance bound to the test substance may be extracted according to the methods of step ii and step iii having been described in section 1-2. (1). The controller 10 stores the extracted optical spectra in the training data database DB1.

In step S16, the controller 10 randomly extracts a predetermined number of optical spectra among from the optical spectra extracted in step S14, and acquires an averaged spectral data set 72 from the extracted predetermined number of optical spectra. The averaged spectral data set 72 may be acquired by the method of step v having been described in section 1-2. (1). The controller 10 stores the acquired averaged spectral data set 72 in the training data database DB1.

In step S18, the controller 10 links the averaged spectral data set 72 acquired in step S16, with the label information 75 that indicates the type of known substance or the monomer sequence of the known substance, and stores the result in the training data database DB1. The label information 75 may be received from the input device 16, or may be received from other computer via the network 99.

In step S21 illustrated in FIG. 10, the controller 10 reads the deep learning algorithm 50 from the algorithm database DB2.

In step S22, the controller 10 inputs the averaged spectral data set 72 acquired in step S16 illustrated in FIG. 9 into the input layer of the deep learning algorithm 50, and inputs the label information 75, having been linked with the averaged spectral data set 72 in step S18, into the output layer of the deep learning algorithm 50. The deep learning algorithm 50 is thus trained.

In step S24, the controller 10 stores the trained deep learning algorithm 50 (60) in the algorithm database DB2.

In a case where there are a large number of optical spectra extracted in step S14, and from which other subset is extractable, the processes in steps S16 to S24 are repeated to further train the deep learning algorithm 50 (60).

2-4. Processing of Analysis Program 134

Figure 11:
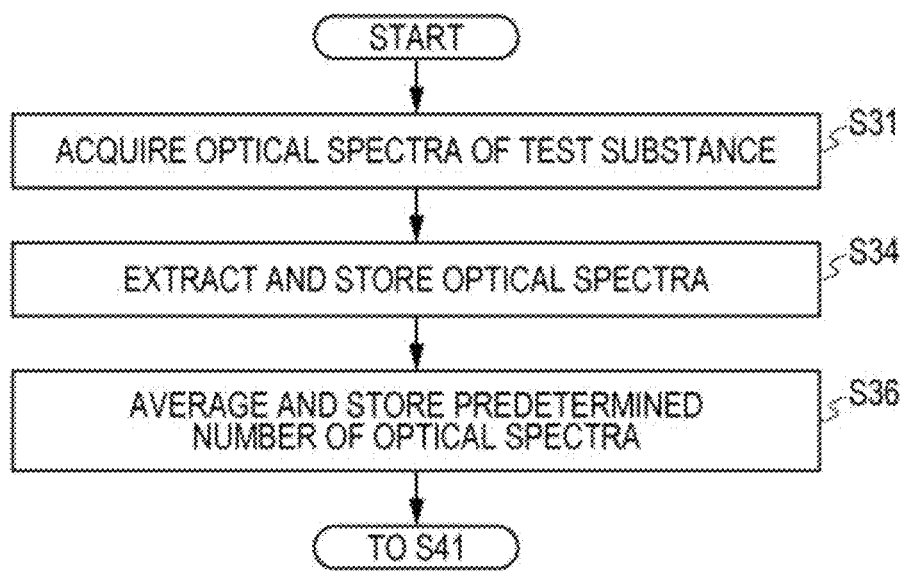
FIG. 11 is a view illustrating a process flow of a first process of an analysis program 134.
Figure 12:
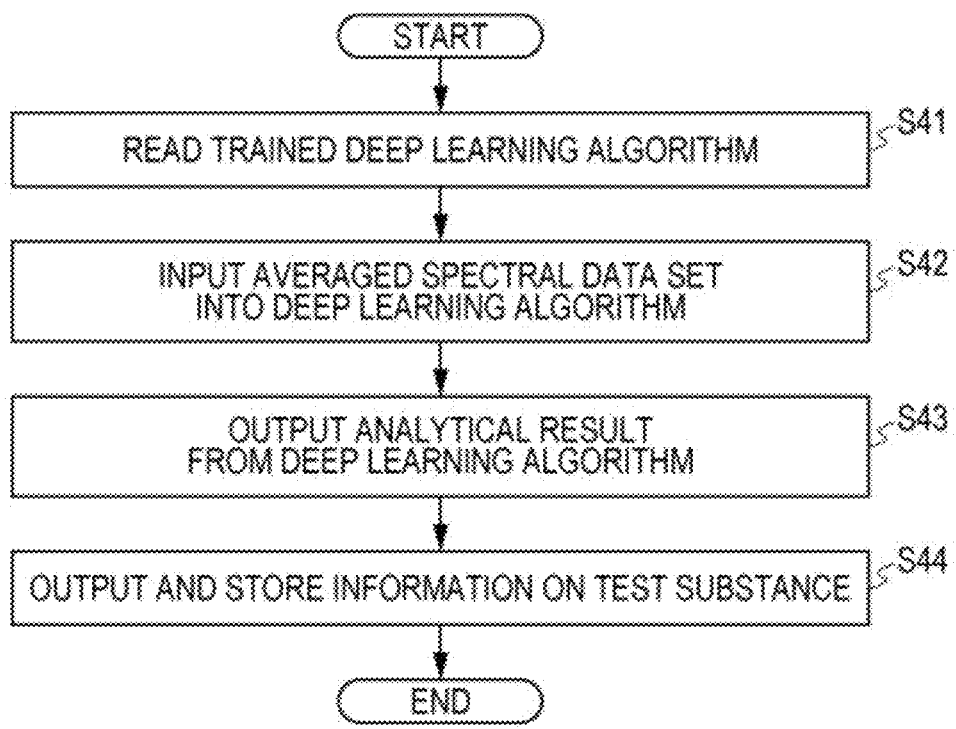
FIG. 12 is a view illustrating a process flow of a second process of the analysis program 134.

FIGS. 11 and 12 illustrate flows of analytical processes for a test substance executed by the controller 10 according to the analysis program 134.

In step S31, the controller 10 acquires a plurality of optical spectra of the measurement sample that contains the substance to be analyzed. More specifically, the controller 10 receives, from the detector 500, data that represents optical spectra detected by the photodetector 560, when the measurement sample that contains the substance to be analyzed is irradiated with the irradiation light (excitation light). In a case where the data that represents the optical spectra is stored in the test data database DB3, the controller 10 acquires the optical spectrum of the known substance by reading the data from the test data database DB3.

In step S34, the controller 10 extracts the optical spectra ascribed to the test substance or a substance bound to the test substance, from the plurality of optical spectra acquired in step S31. The optical spectra ascribed to the test substance or the substance bound to the test substance may be extracted according to the methods of step ii to step iv having been described in section 1-3. The controller 10 stores the extracted optical spectra 80 in the test data database DB3.

In step S36, the controller 10 randomly extracts a predetermined number of optical spectra from among the optical spectra extracted in step S34, and acquires an averaged spectral data set 82 from the extracted predetermined number of optical spectra 80a. The averaged spectral data set 82 may be acquired by the method of step v having been described in section 1-3. The controller 10 stores the acquired averaged spectral data set 82 in the test data database DB3.

Note that the processing in step S34 is omissible. In this case, the controller 10 acquires the averaged spectral data set 82 from the optical spectra acquired in step S31.

In step S41 illustrated in FIG. 12, the controller 10 reads the deep learning algorithm 60 from the algorithm database DB2.

In step S42, the controller 10 inputs the averaged spectral data set 82 acquired in step S36 illustrated in FIG. 11 to the deep learning algorithm 60.

In step S43, the controller 10 outputs an analytical result 85 from the deep learning algorithm 60, and stores the analytical result in the test data database DB3.

In step S44, the controller 10 generates information on the test substance on the basis of the analytical result 85 output from the deep learning algorithm 60, and outputs the information to the output device 17 and/or other computer connected via the network 99. The controller 10 also stores information on the test substance in the test data database DB3. The information on the test substance may be the analytical result 85 in itself, or may be information obtained by editing the analytical result 85.

3. Modified Example

Although section 2. has described an exemplary case where the analyzer 100 takes part in the training of the deep learning algorithm 50 and the analysis of the test substance, the training of the deep learning algorithm 50 and the analysis of the test substance may rely upon any other computer. In this section, an exemplary case where a training device 100A trains the deep learning algorithm 50, and an analyzer 100B analyzes the test substance. Data exchange between the training device 100A and the analyzer 100B is enabled via the media drive 98 or the network 99. The training device 100A and/or the analyzer 100B may be directly connected to the detector 500. The training device 100A and/or the analyzer 100B may acquire data that represents the optical spectra from the detector 500 via the media drive 98 or the network 99. The training device 100A, the analyzer 100B, and the detector 500 may be communicably connected to constitute an analyzer system.

3-1. Training Device 100A

Figure 13:
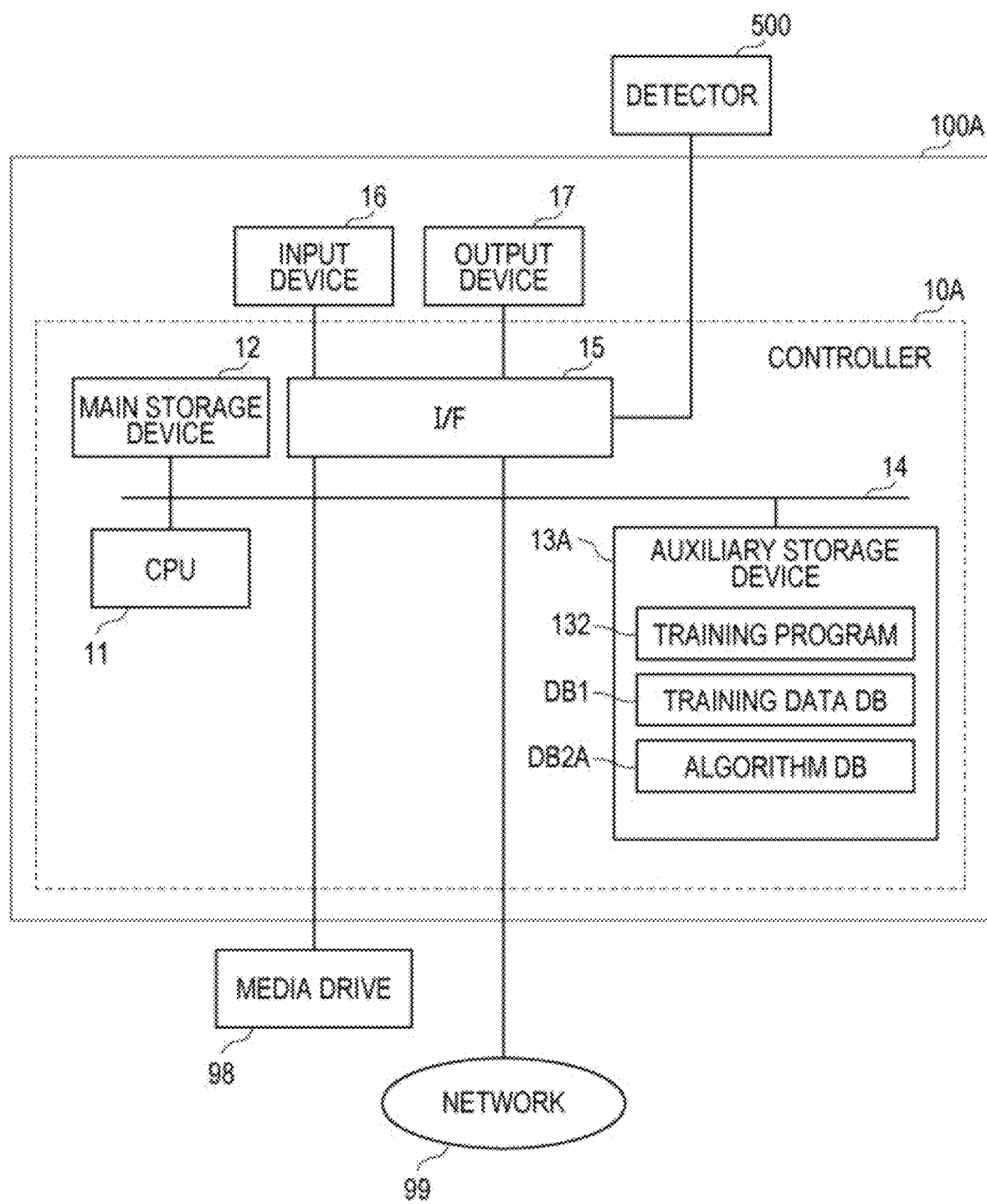
FIG. 13 is a view illustrating the analyzer system 1 and peripheral devices thereof, for explaining a hardware configuration of a training device 100A.

FIG. 13 illustrates a hardware configuration of the training device 100A. The hardware configuration of the training device 100A is basically similar to that of the analyzer 100. The training device 100A has an auxiliary storage device 13A, in place of the auxiliary storage device 13 of the analyzer 100. The auxiliary storage device 13A stores the training program 132, the training data database (DB) DB1, and an algorithm database (DB) DB2A.

Figure 14:
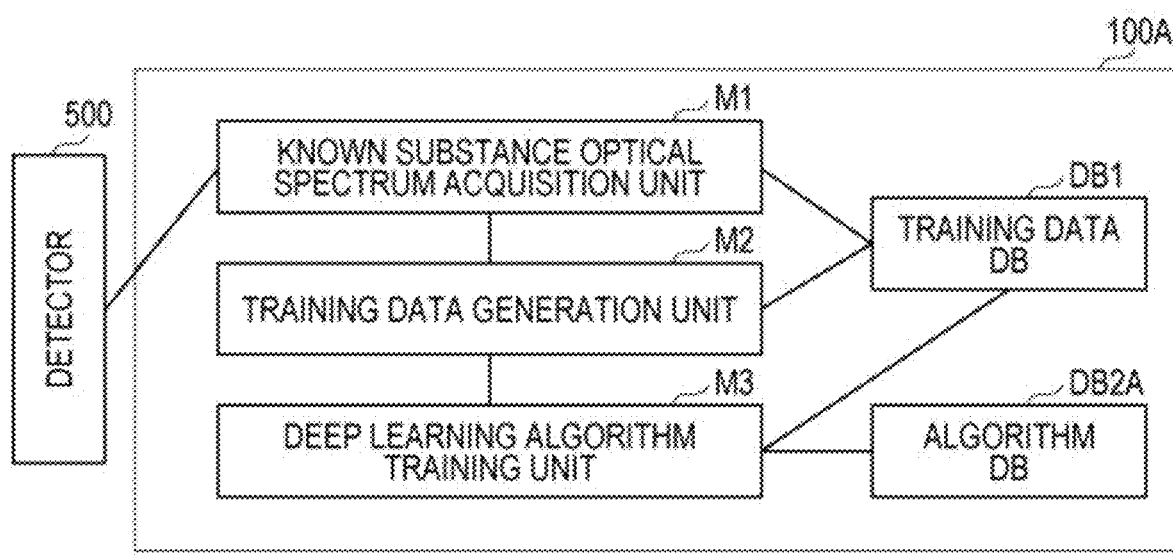
FIG. 14 is a view illustrating the analyzer system 1, for explaining a functional configuration of the training device 100A.

FIG. 14 illustrates a functional configuration of the training device 100A. The training device 100A includes the known substance optical spectrum acquisition unit M1, the training data generation unit M2, the deep learning algorithm training unit M3, the training data database DB1, and the algorithm database DB2A.

A controller 10A of the training device 100A trains the deep learning algorithm 50 according to the training program 132. Although the training at this time employs the process having been described in section 2-3, the present embodiment employs the algorithm database DB2A in place of the algorithm database DB2.

3-2. Analyzer 100B

Figure 15:
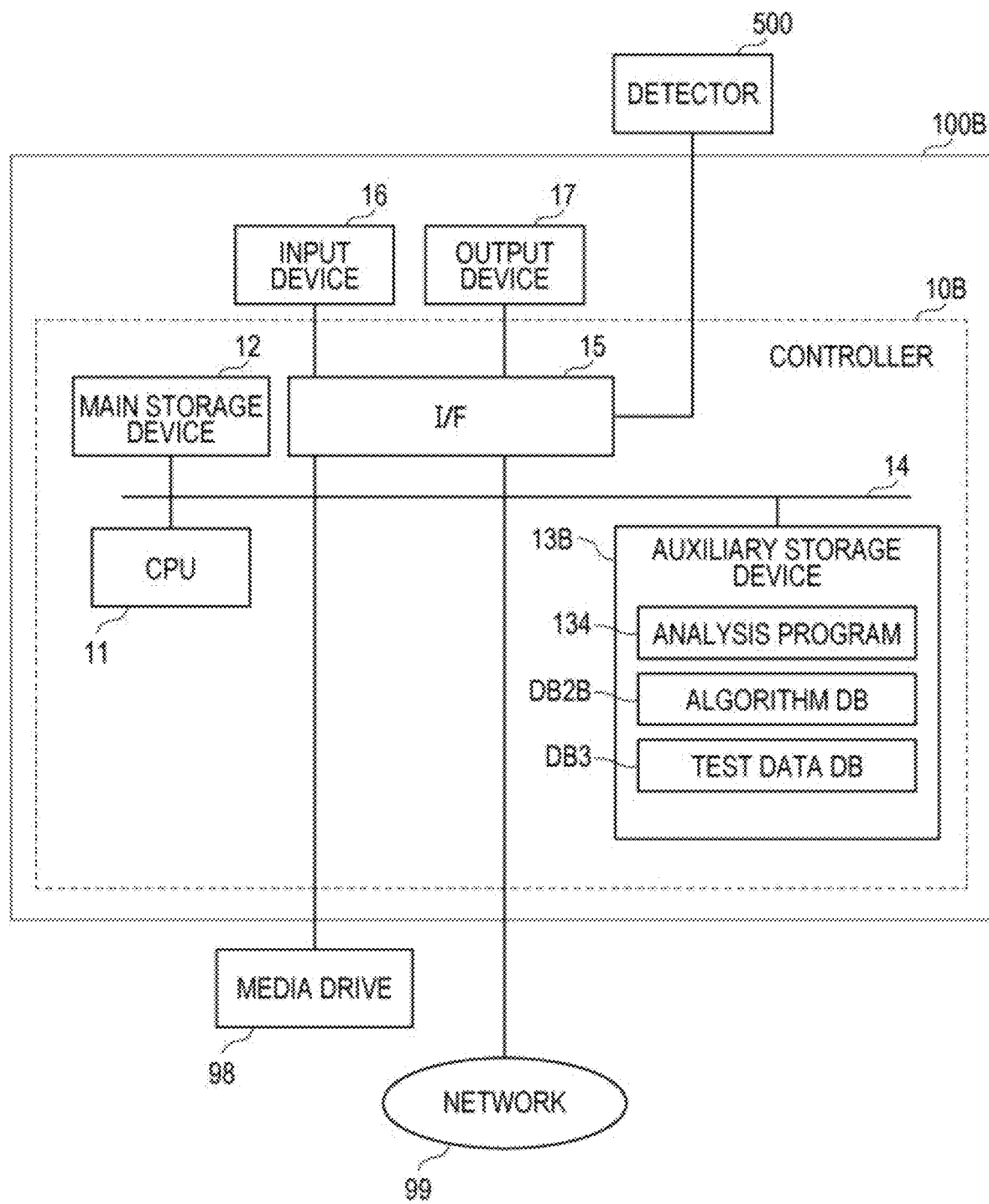
FIG. 15 is a view illustrating the analyzer system 1 and peripheral devices thereof, for explaining a hardware configuration of an analyzer 100B.

FIG. 15 illustrates a hardware configuration of an analyzer 100B. The hardware configuration of the analyzer 100B is basically similar to that of the analyzer 100. The analyzer 100B includes an auxiliary storage device 13B, in place of the auxiliary storage device 13 of the analyzer 100. The auxiliary storage device 13B stores an analysis program 134, an algorithm database (DB) DB2B, and the test data database DB3.

Figure 16:
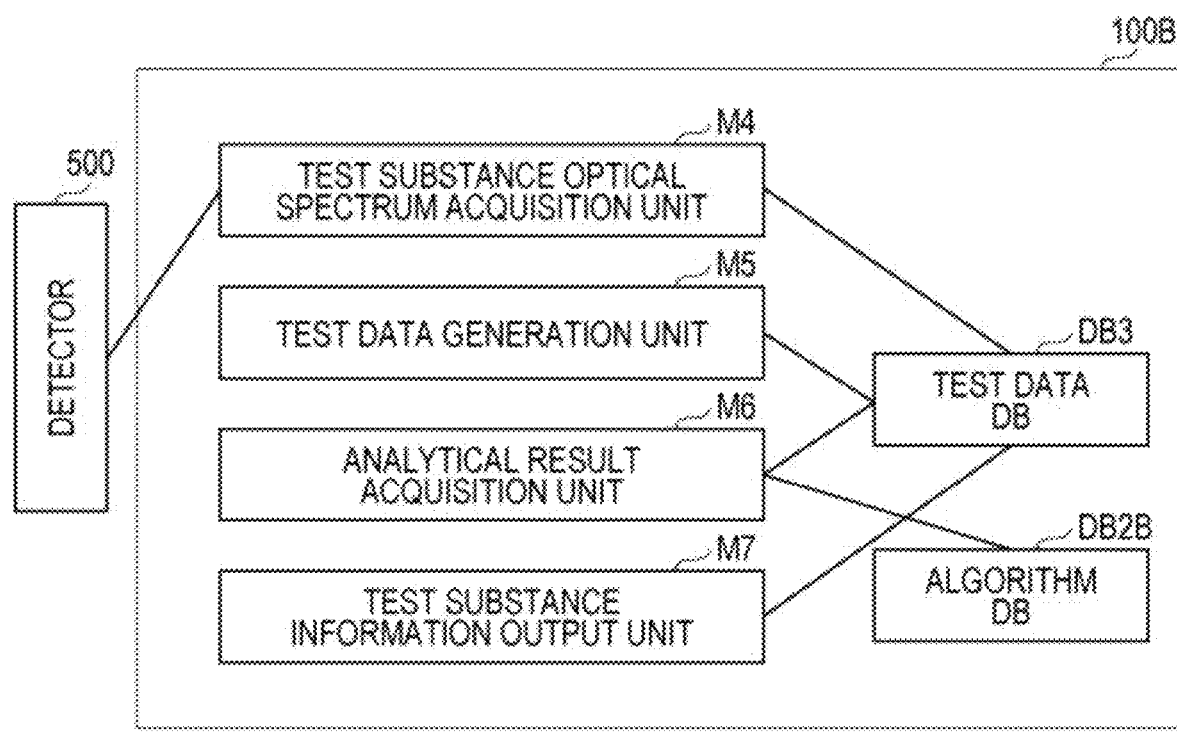
FIG. 16 is a view illustrating the analyzer system 1, for explaining a functional configuration of the analyzer 100B.

FIG. 16 illustrates a functional configuration of the analyzer 100B. The analyzer 100B includes the test substance optical spectrum acquisition unit M4, the test data generation unit M5, the analytical result acquisition unit M6, the test substance information output unit M7, the algorithm database DB2B, and the test data database DB3.

The controller 10B of the analyzer 100B analyzes the test substance according to the analysis program 134 and the deep learning algorithm 60. Although the analysis at this time employs the process having been described in section 2-4, the present embodiment employs the algorithm database DB2B in place of the algorithm database DB2.

4. Storage Medium that Stores Computer Program

The training program 132 and the analysis program 134 may be stored in a storage medium.

That is, each program is stored in a storage medium such as hard disk, semiconductor memory device such as flash memory, or optical disk. Each program may alternatively be stored in a storage medium connectable via a network, such as cloud server. Each program may be provided in a download format, or as a program product stored in a storage medium.

A storage format of the program in the storage medium is not limited as long as the program is readable by the individual devices. The storage in the storage medium is preferably in a nonvolatile manner.

5. Verification of Effect

In order to verify the effect of the analytical method of the present embodiment, the SERS spectra were acquired with use of an aggregate of a metal nanoparticle that contains amino acid, dipeptide, and amyloid β (Aβ), and analytical performances of the analytical method of the present embodiment or a prior method were then compared, on the basis of the spectra.

(1) Prior Method

Each of the optical spectra acquired pixel-wise in step iv having been described in section 1-2. (1) was input into the deep learning algorithm without acquiring the averaged spectral data set, the deep learning algorithm was trained, and analytical performance of the trained deep learning algorithm was verified. Of the plurality of optical spectra, 75% of them was used as the training data, and 25% of them was used as the analytical performance evaluation data.

FIG. 17A shows the number of amino acid training data (numerals in "Training" column) and the number of the analytical performance evaluation data (numerals in "Test" column) in the prior method; FIG. 18A shows the number of dipeptide training data (numerals in "Training column") and the number of analytical performance evaluation data (numerals in "Test" column); and FIG. 19A shows the number of Aβ training data (numerals in "Training" column) and the number of analytical performance evaluation data (numerals in "Test" column). NC represents a negative control to which no sample was added. FIG. 17A lists amino acids in three-letter codes. FIG. 18A lists dipeptides with use of one-letter code amino acids.

(2) Example

Several thousands of optical spectra acquired pixel-wise in step iv having been described in section 1-2. (1) were randomly divided into two groups, one group was directed to the training optical spectra, and the other group was directed to the optical spectra for analytical performance evaluation. One hundred spectra were randomly extracted from the training optical spectra, and then averaged to create one averaged spectral data set. This process was repeated substance-wise, to create 2000 averaged spectral data sets for amino acid, 700 averaged spectral data sets for dipeptide, and 3000 averaged spectral data sets for Aβ. The data sets were input into an unlearned deep learning algorithm together with a label that indicates the substance from which the optical spectra were acquired, to train the deep learning algorithm.

As for Aβ, three spectra were randomly extracted from the training optical spectra, and then averaged to create one averaged spectral data set. This process was repeated substance-wise, to create 3000 averaged spectral data sets. The data sets were input into other unlearned deep learning algorithm together with a label that indicates the substance from which the optical spectra were acquired, to train the deep learning algorithm.

Also for the optical spectra for analytical performance evaluation, 100 spectra were randomly extracted and averaged to create one averaged spectral data set. This process was repeated substance-wise, to create 1000 averaged spectral data sets for amino acid, 350 averaged spectral data sets for dipeptide, and 1500 averaged spectral data sets for Aβ. The data sets were input into the deep learning algorithm trained as described above, to obtain analytical results.

As for Aβ, three spectra were randomly extracted from the training optical spectra, and then averaged to create one averaged spectral data set. This process was repeated substance-wise, to create 1500 averaged spectral data sets. The data sets were input into other deep learning algorithm trained as described above, to obtain analytical results.

FIG. 17B shows the number of amino acid training data (numerals of "Training" column) and the number of analytical performance evaluation data (numerals in "Test" column) in the present embodiment; FIG. 18B shows the number of dipeptide training data (numerals in "Training" column) and the number of analytical performance evaluation data (numerals in "Test" column); and FIG. 19B shows the number of Aβ training data (numerals in "Training" column) and the number of analytical performance evaluation data (numerals in "Test" column), in a case where 100 spectra were used to create the averaged spectral data set. FIG. 19C shows the number of Aβ training data (numerals in "Training" column) and the number of analytical performance evaluation data (numerals in "Test" column), in a case where three spectra were used to create the averaged spectral data set. NC represents a negative control to which no sample was added. FIG. 17B lists amino acids in three-letter codes. FIG. 18B lists dipeptides with use of one-letter code amino acids.

(3) Results

Figure 20:
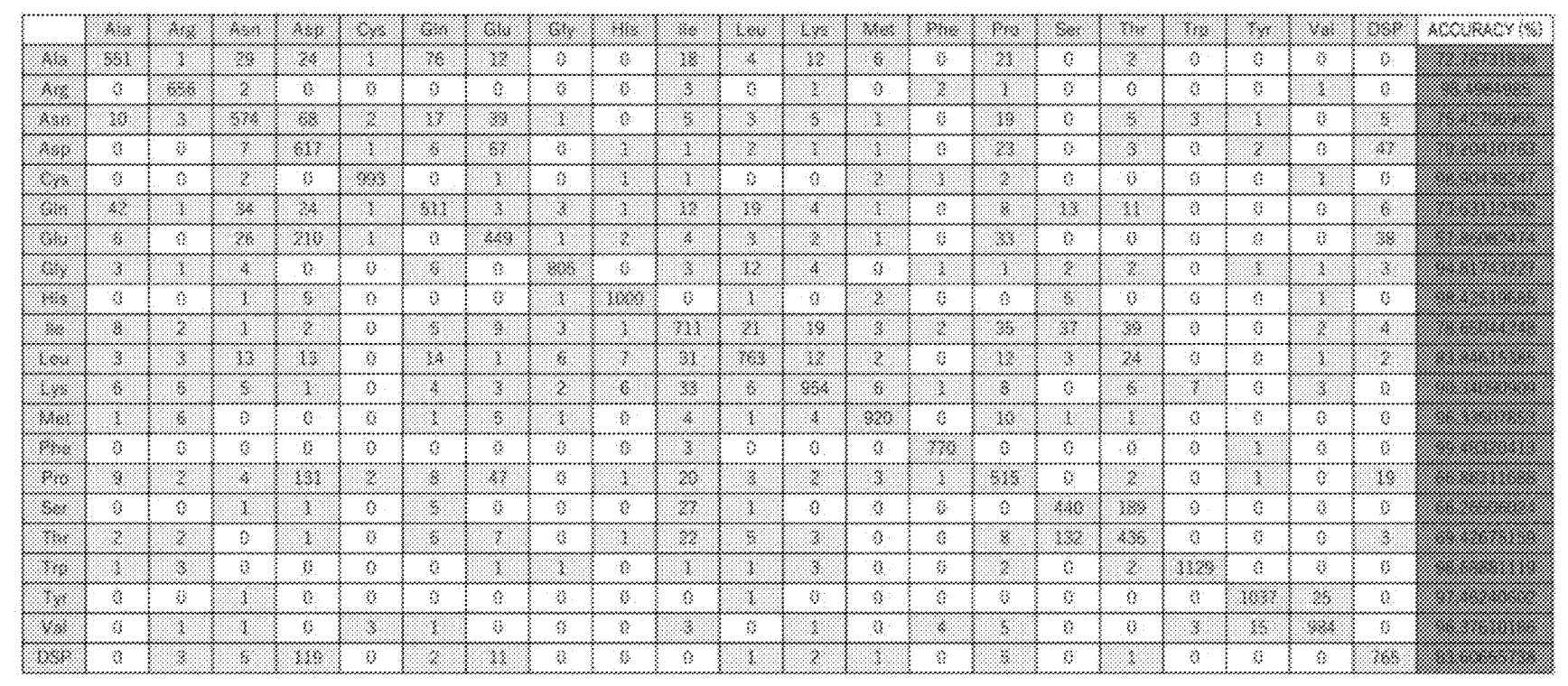
Figure 21:
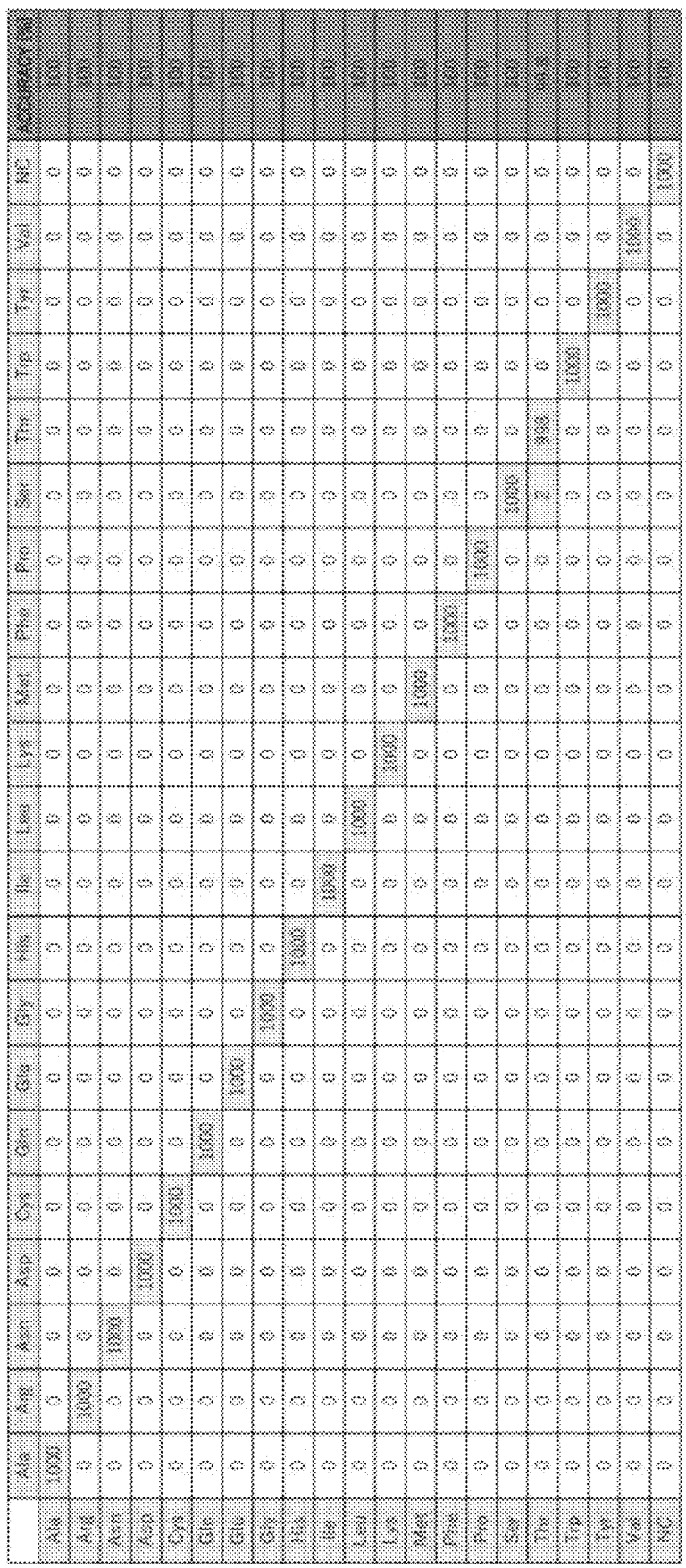
FIG. 21 shows results of Example in a case where the test substance was amino acid.

FIG. 20 shows the result of Comparative Example in a case where the test substance was amino acid. FIG. 21 shows the result of Example in a case where the test substance was amino acid. The accuracy was found to be higher in Example, for all amino acids.

Figure 22:
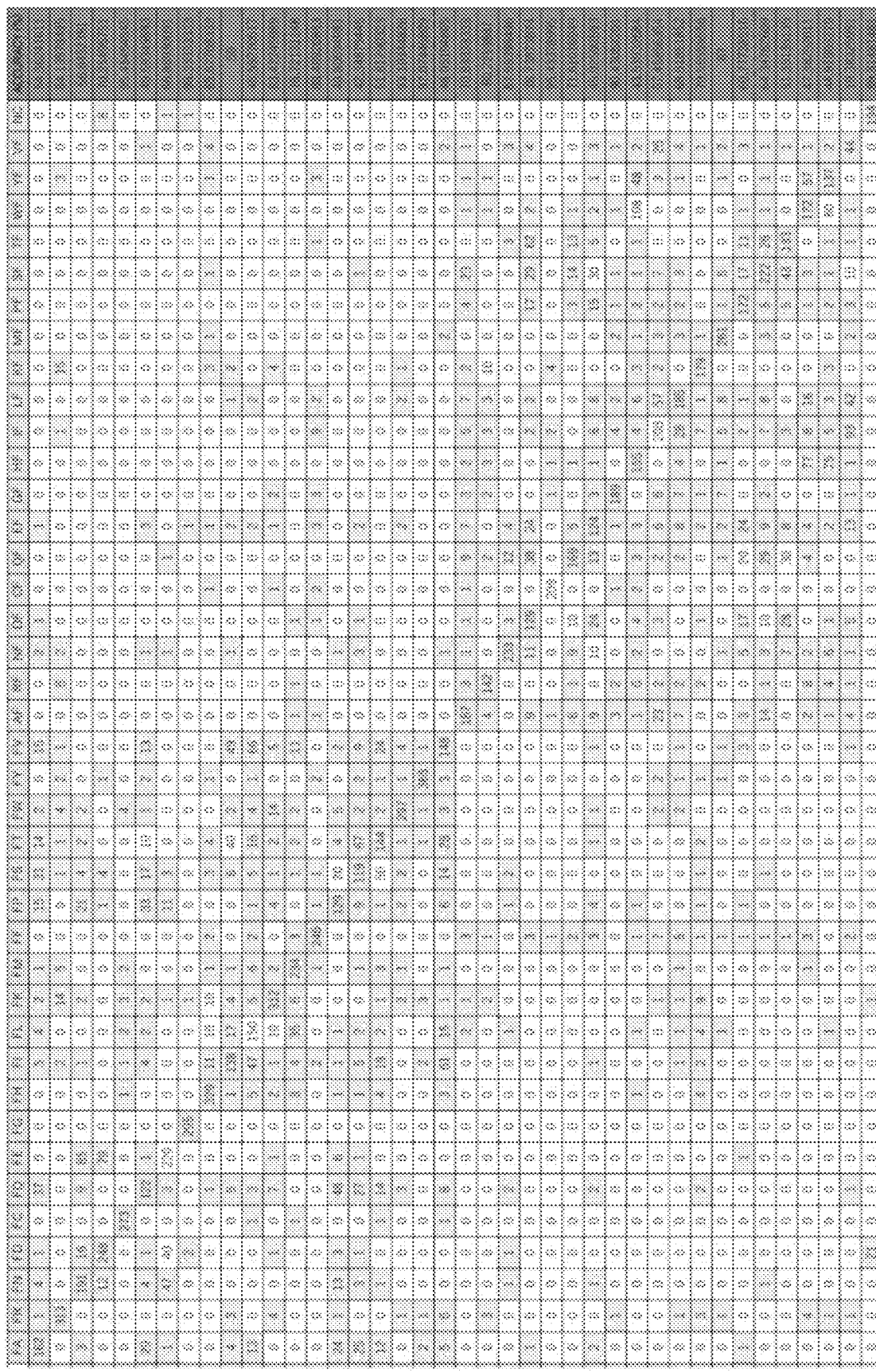
FIG. 22 shows results of Comparative Example that used dipeptides as the test substance.
Figure 23:
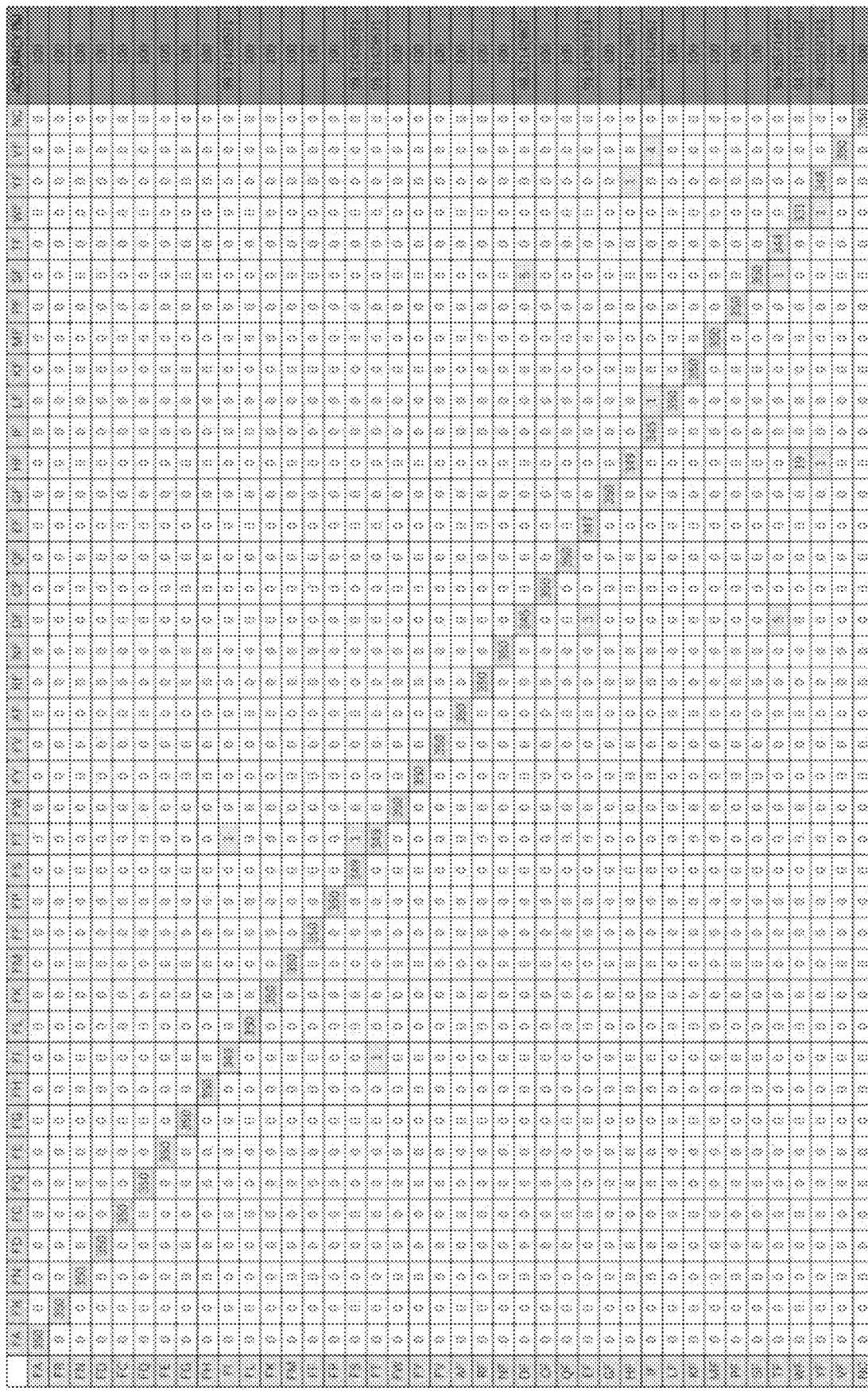
FIG. 23 shows results of Example in a case where the test substance was dipeptide.

FIG. 22 shows the result of Comparative Example in a case where the test substance was dipeptide. FIG. 23 shows the result of Example in a case where the test substance was dipeptide. The accuracy was found to be higher in Example, for all dipeptides.

FIG. 24A shows the result of Comparative Example in a case where the test substance was Aβ. FIG. 24B shows the result of Example in a case where 100 spectra were used to create the averaged spectral data set, and the test substance was Aβ. FIG. 24C shows the result of Example in a case where three spectra were used to create the averaged spectral data set, and the test substance was Aβ. The accuracy was found to be higher in Examples, for all types of Aβ.

The results demonstrated that the analytical method of the present invention can provide higher accuracy of analysis, than the prior method.

What is claimed is:

1. An analytical method for analyzing a test substance contained in a measurement sample, the method comprising:
   generating a data set based on a plurality of optical spectra acquired from a plurality of locations in the measurement sample, a first one of the optical spectra being acquired from a first one of the locations, a second one of the optical spectra being acquired from a second one of the locations;
   inputting the data set into a deep learning algorithm having a neural network structure; and
   outputting information on the test substance, on the basis of an analytical result from the deep learning algorithm,
   wherein the data set is generated by averaging, integrating, multiplying, or dividing signal intensities in a same wavenumber band or a same wavelength band of the plurality of optical spectra,
   wherein the data set is generated by controlling a light source to irradiate the measurement sample and by receiving light from the measurement sample and generating, from the light and on a pixel-by-pixel basis, the plurality of optical spectra acquired from the plurality of locations in the measurement sample, and
   wherein each optical spectrum of the plurality of optical spectra is a Raman spectrum in which each Raman spectrum is a surface-enhanced Raman scattering spectrum.

2. The analytical method according to claim 1, wherein the data set is generated using at least three optical spectra.

3. The analytical method according to claim 1, wherein each optical spectrum of the plurality of optical spectra includes values that indicate signal intensities detected at predetermined wavenumber intervals or predetermined wavelength intervals.

4. The analytical method according to claim 1, wherein the test substance is contained in an aggregate of a metal nanoparticle.

5. The analytical method according to claim 4, wherein the test substance is bound to the metal nanoparticle via a linker.

6. The analytical method according to claim 1, wherein the Raman spectrum is acquired by irradiating the measurement sample in a liquid state with excitation light.

7. The analytical method according to claim 1, wherein the Raman spectrum is acquired by performing placement on a base, drying, and then irradiation with excitation light, for the measurement sample in a liquid state.

8. The analytical method according to claim 1, wherein the output information on the test substance is information that indicates one of known substances as the test substance.

9. The analytical method according to claim 1, wherein the output information on the test substance is information on a sequence of monomers that constitute the test substance.

10. The analytical method according to claim 1, wherein the output information on the test substance is information on a combination of atoms that constitute the test substance.

11. The analytical method according to claim 1, wherein the test substance is at least one selected from the group consisting of amino acid, polypeptide, RNA, DNA, catecholamine, polyamine, and organic acid.

12. The analytical method according to claim 1, wherein the measurement sample that contains the test substance is a sample derived from a living body.

13. The analytical method according to claim 12, wherein the sample derived from a living body is blood, serum, plasma, saliva, ascites, pleural effusion, cerebrospinal fluid, lymph fluid, interstitial fluid, or urine.

14. The analytical method according to claim 1, wherein the neural network is a convolutional neural network.

15. The analytical method according to claim 1, wherein the deep learning algorithm is trained by a data set based on a plurality of optical spectra acquired from a plurality of locations in the measurement sample that contains a known substance.

16. The analytical method according to claim 15, wherein the training data set is input into a deep learning algorithm, while being linked with a label that indicates the known substance.

17. A training method for a deep learning algorithm for analyzing a test substance contained in a measurement sample,
the training method comprising:
generating a data set based on a plurality of optical spectra acquired from a plurality of locations in the measurement sample that contains a known substance whose type, monomer sequence or a combination of atoms has been known, a first one of the optical spectra being acquired from a first one of the locations, a second one of the optical spectra being acquired from a second one of the locations; and
inputting the data set into a deep learning algorithm having a neural network structure, together with label information that indicates the type, the monomer sequence or the combination of atoms of the known substance that corresponds to the data set,
wherein the data set is generated by averaging, integrating, multiplying, or dividing signal intensities in a same wavenumber band or a same wavelength band of the plurality of optical spectra, and
wherein each optical spectrum of the plurality of optical spectra is a Raman spectrum in which each Raman spectrum is a surface-enhanced Raman scattering spectrum.

18. An analyzer for analyzing a test substance contained in a measurement sample,
the analyzer comprising a controller,
wherein the controller is implemented by a processor and is programmed to
generate a data set based on a plurality of optical spectra acquired from a plurality of locations in the measurement sample, a first one of the optical spectra being acquired from a first one of the locations, a second one of the optical spectra being acquired from a second one of the locations,
input the data set into a deep learning algorithm having a neural network structure, and
output information on the test substance, on the basis of an analytical result from the deep learning algorithm,
wherein the data set is generated by averaging, integrating, multiplying, or dividing signal intensities in a same wavenumber band or a same wavelength band of the plurality of optical spectra, and
wherein each optical spectrum of the plurality of optical spectra is a Raman spectrum in which each Raman spectrum is a surface-enhanced Raman scattering spectrum.

19. An analyzer system for analyzing a test substance contained in a measurement sample,
the analyzer system comprising a detector and an analyzer,
wherein the detector includes a light source and a photodetector,
the analyzer includes a controller, and
the controller is implemented by a processor and is programmed to
generate a data set based on a plurality of optical spectra acquired from a plurality of locations in the measurement sample, a first one of the optical spectra being acquired from a first one of the locations, a second one of the optical spectra being acquired from a second one of the locations,
input the data set into a deep learning algorithm having a neural network structure, and
output information on the test substance, on the basis of an analytical result from the deep learning algorithm,
wherein the data set is generated by averaging, integrating, multiplying, or dividing signal intensities in a same wavenumber band or a same wavelength band of the plurality of optical spectra, and
wherein each optical spectrum of the plurality of optical spectra is a Raman spectrum in which each Raman spectrum is a surface-enhanced Raman scattering spectrum.

20. A non-transitory-computer readable medium comprising an analysis program for a test substance contained in a measurement sample, the program being, when run on a computer, designed to execute processes of:
generating a data set based on a plurality of optical spectra acquired from a plurality of locations in the measurement sample, a first one of the optical spectra being acquired from a first one of the locations, a second one of the optical spectra being acquired from a second one of the locations;

inputting the data set into a deep learning algorithm having a neural network structure; and outputting information on the test substance, on the basis of an analytical result from the deep learning algorithm, wherein the data set is generated by averaging, integrating, multiplying, or dividing signal intensities in a same wavenumber band or a same wavelength band of the plurality of optical spectra, and wherein each optical spectrum of the plurality of optical spectra is a Raman spectrum in which each Raman spectrum is a surface-enhanced Raman scattering spectrum.

* * * * *